US012605443B2

(12) United States Patent
Hooper

(10) Patent No.: US 12,605,443 B2
(45) Date of Patent: Apr. 21, 2026

(54) SAR-CoV-2 DNA VACCINE AND METHOD OF ADMINISTERING THEREOF

(71) Applicant: The Government of the United States, as Represented by the Secretary of the Army, Fort Detrick, MD (US)

(72) Inventor: Jay W. Hooper, New Market, MD (US)

(73) Assignee: The Government of the United States, as Represented by the Secretary of the Army, Fort Detrick, MD (US)

( * ) Notice: Subject to any disclaimer, the term of this patent is extended or adjusted under 35 U.S.C. 154(b) by 538 days.

(21) Appl. No.: 18/029,437

(22) PCT Filed: Oct. 13, 2021

(86) PCT No.: PCT/US2021/054784
§ 371 (c)(1),
(2) Date: Mar. 30, 2023

(87) PCT Pub. No.: WO2022/081707
PCT Pub. Date: Apr. 21, 2022

(65) Prior Publication Data
US 2023/0364220 A1    Nov. 16, 2023

(51) Int. Cl.
| | |
|---|---|
| *A61K 39/215* | (2006.01) |
| *A61P 31/14* | (2006.01) |
| *C07K 14/005* | (2006.01) |
| *A61K 39/00* | (2006.01) |

(52) U.S. Cl.
CPC ............ *A61K 39/215* (2013.01); *A61P 31/14* (2018.01); *C07K 14/005* (2013.01); *A61K 2039/53* (2013.01); *A61K 2039/54* (2013.01); *A61K 2039/545* (2013.01); *A61K 2039/575* (2013.01); *C12N 2770/20022* (2013.01); *C12N 2770/20034* (2013.01); *C12N 2770/20071* (2013.01)

(58) Field of Classification Search
None
See application file for complete search history.

(56) References Cited

U.S. PATENT DOCUMENTS

| | | | |
|---|---|---|---|
| 2006/0121580 A1 | 6/2006 | Ter Meulen et al. | |
| 2017/0210697 A1 | 7/2017 | Benenato et al. | |
| 2020/0325182 A1 | 10/2020 | Keller et al. | |

FOREIGN PATENT DOCUMENTS

| | | |
|---|---|---|
| CN | 111088283 A | 5/2020 |
| CN | 111218458 A | 6/2020 |
| WO | WO-9324640 A2 | 12/1993 |
| WO | WO-2015/147899 A1 | 10/2015 |
| WO | WO-2015/148648 A1 | 10/2015 |
| WO | WO-2021/159130 A2 | 8/2021 |

OTHER PUBLICATIONS

Brocato et al. (Viruses, 2019, p. 1-19).*
Barnes et al., "SARS-CoV-2 neutralizing antibody structures inform therapeutic strategies," Nature, vol. 588, pp. 682-702, 2020.
Huang C, et al. Clinical features of patients infected with 2019 novel coronavirus in Wuhan, China. Lancet. 2020;395:497-506.
Lavezzo, E. et al. Suppression of a SARS-CoV-2 outbreak in the Italian municipality of Vo'. Nature 584, 425-429 (2020).
Furukawa, N. W., Brooks, J. T. & Sobel, J. Evidence Supporting Transmission of Severe Acute Respiratory Syndrome Coronavirus 2 While Presymptomatic or Asymptomatic. Emerg Infect Dis Jul. 2020; 26(7): e201595.
World Health Organization, Draft landscape of COVID-19 vaccine candidates (2020).
Cohen J. From mice to monkeys, animals studied for coronavirus answers. Science. 2020;368:221-222.
Chan, J. F. et al. Simulation of the clinical and pathological manifestations of Coronavirus Disease 2019 (COVID-19) in golden Syrian hamster model: implications for disease pathogenesis and transmissibility. 71(9), pp. 2428-2446, Clin Infect Dis. 10.1093/cid/ciaa325 (2020).
Felipe, L. S. et al. A single-dose live-attenuated YF17D-vectored SARS-CoV2 vaccine candidate. Nature. Feb. 2021;590(7845):320-325.
Tostanoski, L. H. et al. Ad26 vaccine protects against SARS-CoV-2 severe clinical disease in hamsters. Nat Med. 2020; 26(11): 1694-1700.
Yahalom-Ronen Y, et al. A single dose of recombinant VSV—?G-spike vaccine provides protection against SARS-CoV-2 challenge. Nat Commun. 2020; 11: 6402.
Brocato, R. L. et al. Disruption of Adaptive Immunity Enhances Disease in SARS-CoV-2 Infected Syrian Hamsters. J Virol. Nov. 2020; 94(22): e01683-20.
Montefiori et al., "Evaluation of Antiviral Drugs and Neutralizing Antibodies to Human Immunodeficiency Virus by a Rapid and Sensitive Microtiter Infection Assay," J. of Clinical Microbiology, 26:231-235, 1988.
Dreyer K., et al. 1999. Primary isolate neutralization by HIV type 1-infected patient sera in the era of highly active antiretroviral therapy. AIDS Res. Hum. Retroviruses 15:1563-1571.
Alving, C.R. et al., Army Liposome Formulation (ALF) family of vaccine adjuvants. Expert Rev. Vaccines 2020, 19(3): 279-292.

(Continued)

*Primary Examiner* — Agnieszka Boesen
(74) *Attorney, Agent, or Firm* — Banner & Witcoff, Ltd.

(57)    ABSTRACT

The current disclosure provides a severe acute respiratory syndrome coronavirus 2 (SARS-CoV-2) spike-based DNA vaccine capable of eliciting immune response to a SARS-CoV-2 in a human subject upon administration. Also provided is a method of eliciting an immune response to a SARS-CoV-2 in a human subject by administering the SARS-CoV-2 spike-based DNA vaccine, for example, intramuscularly using a jet injector.

14 Claims, 14 Drawing Sheets
Specification includes a Sequence Listing.

(56) References Cited

OTHER PUBLICATIONS

O'Hagan, D.T. et al., MF59 adjuvant: the best insurance against influenza strain diversity. Expert Rev Vaccines 2011; 10:447-462.

Case JB, et al. Neutralizing Antibody and Soluble ACE2 Inhibition of a Replication-Competent VSV-SARS-CoV-2 and a Clinical Isolate of SARS-CoV-2. Cell Host Microbe. 2020;28:475-485.

Brocato, R.L. et al., A Lethal Disease Model for Hantavirus Pulmonary Syndrome in Immunosuppressed Syrian Hamsters Infected with Sin Nombre Virus. J. Virol. 2014, 88(2):811-9.

Kwilas S, et al. A hantavirus pulmonary syndrome (HPS) DNA vaccine delivered using a spring-powered jet injector elicits a potent neutralizing antibody response in rabbits and nonhuman primates. Curr. Gene Ther. 2014;14:200-210.

Liu J, et al. Molecular detection of SARS-CoV-2 in formalin fixed paraffin embedded specimens. JCI Insight. Jun. 18, 2020; 5(12): e139042.

Brocato, R. L. & Hooper, J. W. Progress on the Prevention and Treatment of Hantavirus Disease. Viruses. Jul. 2019; 11(7): 610.

Yu J, et al. DNA vaccine protection against SARS-CoV-2 in rhesus macaques. Science. Aug. 14, 2020; 369(6505): 806-811.

De Alwis, R. et al. A Single Dose of Self-Transcribing and Replicating RNA Based SARS-CoV-2 Vaccine Produces Protective Adaptive Immunity In Mice. Mol Ther. Jun. 2, 2021;29(6):1970-1983.

Case JB, et al. Replication-Competent Vesicular Stomatitis Virus Vaccine Vector Protects against SARS-CoV-2-Mediated Pathogenesis in Mice. Cell Host Microbe. 2020;28:465-474.

Mercado, N. B. et al. Single-shot Ad26 vaccine protects against SARS-CoV-2 in rhesus macaques. Nature. Oct. 2020; 586(7830): 583-588.

Sun, W. et al. A Newcastle disease virus (NDV) expressing membrane-anchored spike as a cost-effective inactivated SARS-CoV-2 vaccine. Vaccines (Basel). Dec. 2020; 8(4): 771.

Smith TRF, et al. Immunogenicity of a DNA vaccine candidate for COVID-19. Nat. Commun. 2020;11:2601.

Brocato, R. L. et al. Small animal jet injection technique results in enhanced immunogenicity of hantavirus DNA vaccines. Vaccine. Feb. 12, 2021;39(7):1101-1110.

Brocato, R. L. et al., Protective efficacy of a SARS-CoV-2 DNA vaccine in wild-type and immunosuppressed Syrian hamsters. NPJ Vaccines. Jan. 25, 2021;6(1):16.

International Search Report and Written Opinion mailed Feb. 2, 2022 in PCT/US2021/054784.

* cited by examiner

FIG. 3A                    FIG. 3B
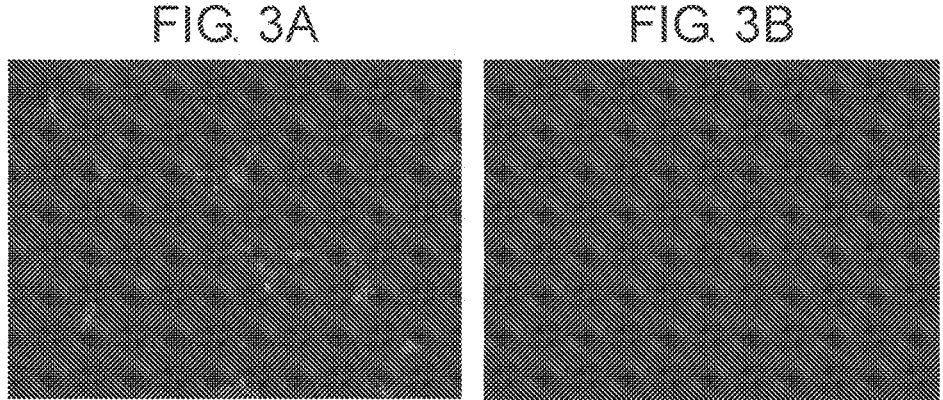

SEQUENCE LISTING

```
<160> NUMBER OF SEQ ID NOS: 7

<210> SEQ ID NO 1
<211> LENGTH: 3822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgtttgtgt ttctggtcct cctccccctc gtgagctccc agtgcgtcaa tctgaccaca        60
agaacacagc tccccccgc ctacacaaat agcttcacaa ggggcgtgta ctaccccgat       120
aaggtgttta ggtccagcgt cctccacagc acacaagacc tcttcctccc cttctttccc       180
aacgtgacat ggtttcatgc cattcacgtg agcggcacaa acggcaccaa aagattcgac       240
aaccccgtgc tccccttttaa tgacggagtc tacttcgcca gcaccgagaa aagcaacatc       300
atcagaggct ggatcttcgg aacaacactc gactccaaaa cccagtctct gctcattgtc       360
aacaatgcca ccaacgtggt gatcaaggtc tgtgagttcc agttttgtaa cgatcccttt       420
ctgggagtgt actatcataa aaacaataag agctggatgg agtccgagtt tagggtctac       480
tccagcgcca ataactgtac cttcgagtac gtgagccaac cctttctgat ggacctcgag       540
ggaaagcaag gcaacttcaa gaatctgaga gagttcgtgt tcaagaatat cgacggctat       600
tttaaaattt atagcaaaca taccccatc aacctcgtga gggatctgcc ccaaggcttc       660
tccgctctcg aacctctcgt ggacctccct attggcatca acatcaccag attccagacc       720
ctcctcgctc tgcatagaag ctatctgacc cccggagatt ccagctccgg ctggacagcc       780
ggagctgctg cctactacgt gggatatctg cagcctagga catttctgct gaaatacaat       840
gagaatggca ccatcaccga tgctgtcgat tgtgctctgg accctctgag cgagaccaag       900
tgtaccctca agagcttcac cgtcgagaag ggaatttatc aaaccagcaa ctttagagtc       960
cagcccaccg aaagcatcgt gaggttcccc aacatcacaa acctctgccc cttcggagag      1020
gtcttcaatg ctacaagatt cgctagcgtg tacgcttgga atagaaagag aatctccaac      1080
tgcgtggccg actattccgt gctgtataac agcgcctcct ttagcacctt taagtgctac      1140
ggcgtgtccc ctacaaaact gaacgatctc tgcttcacca acgtgtacgc cgacagcttc      1200
gtgattagag agatgaggt cagacagatt gctcccggcc aaaccggcaa gatcgccgac      1260
tataattaca gctccccga cgacttcacc ggatgcgtca tcgcttggaa cagcaacaat      1320
ctggacagca aagtgggcgg caattacaac tatctgtata ggctgttcag aaagagcaat      1380
ctcaagccct cgagagaga catcagcaca gaaatctacc aagctggcag cacccccttgc      1440 aacggcgtgg agggcttcaa ttgctacttc ccctccaaa gctacggctt ccagcccaca      1500
aacggagtgg gctaccagcc ttataggtg gtggtgctga gctttgagct gctgcatgcc      1560
```

-continued

```
cccgccaccg tctgtggacc caagaaatcc accaatctgg tgaaaaataa gtgcgtgaat    1620
tttaacttca atggactcac cggaaccgga gtcctcaccg agagcaacaa aaagtttctg    1680
cccttccaac aattcggaag agacatcgct gacaccaccg atgccgtgag ggacccccaa    1740
acactggaga tcctcgatat caccccttgc agcttcggag gagtgagcgt catcacaccc    1800
ggaacaaata cctccaacca agtggccgtg ctctaccaag acgtcaactg tacagaagtg    1860
cccgtggcca ttcacgccga ccagctcacc cccacatgga gagtgtatag caccggctcc    1920
aatgtgtttc agacaagagc cggatgtctg atcggagctg aacacgtcaa caactcctat    1980
gagtgcgaca tccctatcgg agctggaatt tgcgccagct accagaccca gaccaattcc    2040
cctaggaggg ccagatccgt cgcctcccag tccatcatcg cctataccat gtccctcgga    2100
gctgagaaca gcgtcgccta tagcaacaac tccatcgcca tccccaccaa ctttacaatc    2160
agcgtcacca ccgagattct gcccgtgagc atgaccaaaa ccagcgtcga ctgcaccatg    2220
tacatctgcg gagatagcac agagtgcagc aatctgctgc tgcagtacgg atccttctgc    2280
acacagctca ataggcccct caccggcatc gctgtggagc aagataagaa cacacaagag    2340
gtgttcgctc aagtgaaaca gatttataaa acccctccca tcaaggactt cggaggattc    2400
aacttctccc aaatcctccc cgaccccagc aagcctagca gagaggagctt catcgaggat    2460 ctgctgttca acaaggtgac cctcgccgat gccggcttca tcaaacagta cggcgactgt    2520
ctgggagata tcgccgctag ggatctgatc tgtgctcaga agttcaacgg cctcaccgtg    2580
ctgcctcctc tgctgaccga cgagatgatc gcccagtata cctccgctct gctggctgga    2640
acaattacct ccggatggac attcggagct ggagccgctc tgcaaatccc ctttgccatg    2700
cagatggcct ataggttcaa tggcatcggc gtcacccaga cgtgctgta tgaaaaccag    2760 aaactgattg ccaaccagtt caatagcgcc atcggcaaaa tccaagacag cctctcctcc    2820
acagcttccg ctctcggaaa actgcaagac gtcgtgaacc aaaatgccca gccctcaac    2880 acactggtga agcagctctc cagcaacttt ggagctatct ccagcgtgct gaacgatatt    2940
ctgtctagac tggataaagt cgaggccgag gtgcaaatcg atagactgat caccggcaga    3000
ctccagtctc tgcaaacta tgtgacccag caactcatta gggccgccga gatcagagcc    3060
tccgccaatc tggccgctac aaagatgagc gagtgcgtgc tgggccaatc caagagagtg    3120
gacttctgtg gcaagggcta tcatctcatg agcttccccc aatccgcccc tcatggcgtg    3180
gtcttcctcc atgtgaccta cgtccccgcc caagagaaga acttcacaac agctcccgcc    3240
atctgccatg atggcaaggc tcatttcccc agagaaggcg tgtttgtgtc caatggcaca    3300
cactggttcg tcacccagag gaatttctat gaaccccaga tcatcaccac cgacaacacc    3360
ttcgtctccg gcaactgcga tgtggtcatc ggcatcgtga caacacagt gtatgaccct    3420 ctccaacccg agctggacag cttcaaggag gagctcgata atatttttaa gaaccataca    3480
tcccccgacg tggacctcgg cgacatcagc ggcattaacg ccagcgtggt gaacatccag    3540
aaggagatcg ataggctcaa cgaggtggcc aagaatctga cgaaagcct catcgatctg    3600 caagagctcg gcaagtacga gcagtacatc aagtggcctt ggtacatctg gctcggcttt    3660
attgccggac tgatcgctat cgtcatggtg accatcatgc tgtgctgcat gacaagctgc    3720
tgtagctgtc tgaaaggctg ttgtagctgc ggaagctgct gcaagttcga tgaggacgac    3780
agcgagcccg tgctgaaggg cgtgaagctg cactacacat ag                       3822
```

<210> SEQ ID NO 2
<211> LENGTH: 1273

```
<212> TYPE: PRT
<213> ORGANISM: Severe acute respiratory syndrome coronavirus 2

<400> SEQUENCE: 2

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
        50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
        290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
        370                 375                 380

Thr Lys Leu Asn Asp Leu Cys Phe Thr Asn Val Tyr Ala Asp Ser Phe
385                 390                 395                 400
```

-continued

```
Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
            530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815
```

```
Phe Ile Glu Asp Leu Leu Phe Asn Lys Val Thr Leu Ala Asp Ala Gly
        820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
        850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
1010                1015                1020

Leu Ala  Ala Thr Lys Met Ser  Glu Cys Val Leu Gly  Gln Ser Lys
1025                1030                1035

Arg Val  Asp Phe Cys Gly Lys  Gly Tyr His Leu Met  Ser Phe Pro
1040                1045                1050

Gln Ser  Ala Pro His Gly Val  Val Phe Leu His Val  Thr Tyr Val
1055                1060                1065

Pro Ala  Gln Glu Lys Asn Phe  Thr Thr Ala Pro Ala  Ile Cys His
1070                1075                1080

Asp Gly  Lys Ala His Phe Pro  Arg Glu Gly Val Phe  Val Ser Asn
1085                1090                1095

Gly Thr  His Trp Phe Val Thr  Gln Arg Asn Phe Tyr  Glu Pro Gln
1100                1105                1110

Ile Ile  Thr Thr Asp Asn Thr  Phe Val Ser Gly Asn  Cys Asp Val
1115                1120                1125

Val Ile  Gly Ile Val Asn Asn  Thr Val Tyr Asp Pro  Leu Gln Pro
1130                1135                1140

Glu Leu  Asp Ser Phe Lys Glu  Glu Leu Asp Lys Tyr  Phe Lys Asn
1145                1150                1155

His Thr  Ser Pro Asp Val Asp  Leu Gly Asp Ile Ser  Gly Ile Asn
1160                1165                1170

Ala Ser  Val Val Asn Ile Gln  Lys Glu Ile Asp Arg  Leu Asn Glu
1175                1180                1185

Val Ala  Lys Asn Leu Asn Glu  Ser Leu Ile Asp Leu  Gln Glu Leu
1190                1195                1200

Gly Lys  Tyr Glu Gln Tyr Ile  Lys Trp Pro Trp Tyr  Ile Trp Leu
1205                1210                1215

Gly Phe  Ile Ala Gly Leu Ile  Ala Ile Val Met Val  Thr Ile Met
```

```
          1220            1225            1230

Leu Cys  Cys Met Thr Ser Cys  Cys Ser Cys Leu Lys  Gly Cys Cys
    1235            1240            1245

Ser Cys  Gly Ser Cys Cys Lys  Phe Asp Glu Asp Asp  Ser Glu Pro
    1250            1255            1260

Val Leu  Lys Gly Val Lys Leu  His Tyr Thr
    1265            1270

<210> SEQ ID NO 3
<211> LENGTH: 6
<212> TYPE: DNA
<213> ORGANISM: Unknown
<220> FEATURE:
<223> OTHER INFORMATION: Description of Unknown:
      Kozak sequence

<400> SEQUENCE: 3 gccacc                                                                 6

<210> SEQ ID NO 4
<211> LENGTH: 8058
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gggggggggg ggcgctgagg tctgcctcgt gaagaaggtg ttgctgactc ataccaggcc      60
tgaatcgccc catcatccag ccagaaagtg agggagccac ggttgatgag agctttgttg     120
taggtggacc agttggtgat tttgaacttt tgctttgcca cggaacggtc tgcgttgtcg     180
ggaagatgcg tgatctgatc cttcaactca gcaaaagttc gatttattca acaaagccgc     240
cgtcccgtca agtcagcgta atgctctgcc agtgttacaa ccaattaacc aattctgatt     300
agaaaaactc atcgagcatc aaatgaaact gcaatttatt catatcagga ttatcaatac     360
catatttttg aaaaagccgt ttctgtaatg aaggagaaaa ctcaccgagg cagttccata     420
ggatggcaag atcctggtat cggtctgcga ttccgactcg tccaacatca atacaaccta     480
ttaatttccc ctcgtcaaaa ataaggttat caagtgagaa atcaccatga gtgacgactg     540
aatccggtga gaatggcaaa agcttatgca tttctttcca gacttgttca acaggccagc     600
cattacgctc gtcatcaaaa tcactcgcat caaccaaacc gttattcatt cgtgattgcg     660
cctgagcgag acgaaatacg cgatcgctgt taaaaggaca attacaaaca ggaatcgaat     720
gcaaccggcg caggaacact gccagcgcat caacaatatt ttcacctgaa tcaggatatt     780
cttctaatac ctggaatgct gttttcccgg ggatcgcagt ggtgagtaac catgcatcat     840
caggagtacg gataaaatgc ttgatggtcg gaagaggcat aaattccgtc agccagttta     900
gtctgaccat ctcatctgta acatcattgg caacgctacc tttgccatgt ttcagaaaca     960
actctggcgc atcgggcttc ccatacaatc gatagattgt cgcacctgat tgcccgacat    1020
tatcgcgagc ccatttatac ccatataaat cagcatccat gttggaattt aatcgcggcc    1080
tcgagcaaga cgtttcccgt tgaatatggc tcataacacc ccttgtatta ctgtttatgt    1140
aagcagacag ttttattgtt catgatgata tattttatc ttgtgcaatg taacatcaga    1200
gattttgaga cacaacgtgg ctttcccccc cccccggca tgcctgcagg tcgacataaa    1260
tcaatattgg ctattggcca ttgcatacgt tgtatctata tcataatatg tacatttata    1320
```

```
ttggctcatg tccaatatga ccgccatgtt gacattgatt attgactagt tattaatagt  1380
aatcaattac ggggtcatta gttcatagcc catatatgga gttccgcgtt acataactta  1440
cggtaaatgg cccgcctcgt daccgcccaa cgacccccgc ccattgacgt caataatgac  1500
gtatgttccc atagtaacgc aatagggac tttccattga cgtcaatggg tggagtattt  1560
acggtaaact gcccacttgg cagtacatca agtgtatcat atgccaagtc cggcccccta  1620
ttgacgtcaa tgacggtaaa tggcccgcct ggcattatgc ccagtacatg accttacggg  1680
actttcctac ttggcagtac atctacgtat tagtcatcgc tattaccatg gtgatgcggt  1740
tttggcagta caccaatggg cgtggatagc ggtttgactc acggggattt ccaagtctcc  1800
accccattga cgtcaatggg agtttgtttt ggcaccaaaa tcaacgggac tttccaaaat  1860
gtcgtaataa ccccgccccg ttgacgcaaa tgggcggtag gcgtgtacgg tgggaggtct  1920
atataagcag agctcgttta gtgaaccgtc agatcgcctg gagacgccat ccacgctgtt  1980
ttgacctcca tagaagacac cgggaccgat ccagcctccg cggccgggaa cggtgcattg  2040
gaacgcggat tccccgtgcc aagagtgacg taagtaccgc ctatagactc tataggcaca  2100
cccctttggc tcttatgcat gctatactgt ttttggcttg gggcctatac accccgctc  2160 cttatgctat aggtgatggt atagcttagc ctataggtgt gggttattga ccattattga  2220
ccactcccct attggtgacg atactttcca ttactaatcc ataacatggc tctttgccac  2280
aactatctct attggctata tgccaatact ctgtccttca gagactgaca cggactctgt  2340
atttttacag gatggggtcc catttattat ttacaaattc acatatacaa caacgccgtc  2400
ccccgtgccc gcagttttta ttaaacatag cgtgggatct ccacgcgaat ctcgggtacg  2460
tgttccggac atgggctctt ctccggtagc ggcggagctt ccacatccga gccctggtcc  2520
catgcctcca gcggctcatg gtcgctcggc agctccttgc tcctaacagt ggaggccaga  2580
cttaggcaca gcacaatgcc caccaccacc agtgtgccgc acaaggccgt ggcggtaggg  2640
tatgtgtctg aaaatgagct cggagattgg gctcgcaccg tgacgcagat ggaagactta  2700
aggcagcggc agaagaagat gcaggcagct gagttgttgt attctgataa gagtcagagg  2760
taactcccgt tgcggtgctg ttaacggtgg agggcagtg agtctgagca gtactcgttg  2820
ctgccgcgcg cgccaccaga cataatagct gacagactaa cagactgttc ctttccatgg  2880
gtcttttctg cagtcaccgt ccaagcttgc ggccgcgcca ccatgtttgt gtttctggtc  2940 ctcctcccc tcgtgagctc ccagtgcgtc aatctgacca caagaacaca gctcccccc  3000 gcctacacaa atagcttcac aaggggcgtg tactaccccg ataaggtgtt taggtccagc  3060
gtcctccaca gcacacaaga cctcttcctc cccttctttt ccaacgtgac atggtttcat  3120
gccattcacg tgagcggcac aaacggcacc aaaagattcg acaacccgt gctcccctt  3180 aatgacggag tctacttcgc cagcaccgag aaaagcaaca tcatcagagg ctggatcttc  3240
ggaacaacac tcgactccaa aacccagtct ctgctcattg tcaacaatgc caccaacgtg  3300
gtgatcaagg tctgtgagtt ccagttttgt aacgatccct ttctgggagt gtactatcat  3360
aaaaacaata agagctggat ggagtccgag tttagggtct actccagcgc caataactgt  3420
accttcgagt acgtgagcca acccttctg atggacctcg agggaaagca aggcaacttc  3480
aagaatctga gagagttcgt gttcaagaat atcgacggct attttaaaat ttatagcaaa  3540 catacccca tcaacctcgt gagggatctg ccccaaggct ctccgctct cgaacctctc  3600 gtggacctcc ctattggcat caacatcacc agattccaga ccctcctcgc tctgcataga  3660
agctatctga cccccggaga ttccagctcc ggctggacag ccggagctgc tgcctactac  3720
```

-continued

```
gtgggatatc tgcagcctag gacatttctg ctgaaataca atgagaatgg caccatcacc   3780
gatgctgtcg attgtgctct ggaccctctg agcgagacca agtgtaccct caagagcttc   3840
accgtcgaga agggaattta tcaaaccagc aactttagag tccagcccac cgaaagcatc   3900
gtgaggttcc ccaacatcac aaacctctgc cccttcggag aggtcttcaa tgctacaaga   3960
ttcgctagcg tgtacgcttg gaatagaaag agaatctcca actgcgtggc cgactattcc   4020
gtgctgtata acagcgcctc ctttagcacc tttaagtgct acggcgtgtc ccctacaaaa   4080
ctgaacgatc tctgcttcac caacgtgtac gccgacagct tcgtgattag aggagatgag   4140
gtcagacaga ttgctcccgg ccaaaccggc aagatcgccg actataatta caagctcccc   4200
gacgacttca ccggatgcgt catcgcttgg aacagcaaca atctggacag caaagtgggc   4260
ggcaattaca actatctgta taggctgttc agaaagagca atctcaagcc cttcgagaga   4320
gacatcagca cagaaatcta ccaagctggc agcacccctt gcaacggcgt ggagggcttc   4380
aattgctact ccccctcca aagctacggc ttccagccca caaacggagt gggctaccag   4440
ccttataggg tggtggtgct gagctttgag ctgctgcatg cccccgccac cgtctgtgga   4500
cccaagaaat ccaccaatct ggtgaaaaat aagtgcgtga attttaactt caatggactc   4560
accggaaccg gagtcctcac cgagagcaac aaaaagtttc tgcccttcca acaattcgga   4620
agagacatcg ctgacaccac cgatgccgtg agggaccccc aaacactgga gatcctcgat   4680
atcacccctt gcagcttcgg aggagtgagc gtcatcacac ccggaacaaa tacctccaac   4740
caagtggccg tgctctacca agacgtcaac tgtacagaag tgcccgtggc cattcacgcc   4800
gaccagctca cccccacatg gagagtgtat agcaccggct ccaatgtgtt tcagacaaga   4860
gccggatgtc tgatcggagc tgaacacgtc aacaactcct atgagtgcga catccctatc   4920
ggagctggaa tttgcgccag ctaccagacc cagaccaatt cccctaggag ggccagatcc   4980
gtcgcctccc agtccatcat cgcctatacc atgtccctcg gagctgagaa cagcgtcgcc   5040
tatagcaaca actccatcgc catccccacc aactttacaa tcagcgtcac caccgagatt   5100
ctgcccgtga gcatgaccaa aaccagcgtc gactgcacca tgtacatctg cggagatagc   5160
acagagtgca gcaatctgct gctgcagtac ggatccttct gcacacagct caatagggcc   5220
ctcaccggca tcgctgtgga gcaagataag aacacacaag aggtgttcgc tcaagtgaaa   5280
cagatttata aaacccctcc catcaaggac ttcggaggat tcaacttctc ccaaatcctc   5340
cccgacccca gcaagcctag caagaggagc ttcatcgagg atctgctgtt caacaaggtg   5400
accctcgccg atgccggctt catcaaacag tacggcgact gtctgggaga tatcgccgct   5460
agggatctga tctgtgctca gaagttcaac ggcctcaccg tgctgcctcc tctgctgacc   5520
gacgagatga tcgcccagta tacctccgct ctgctggctg aacaattac ctccggatgg   5580 acattcggag ctggagccgc tctgcaaatc cccttgcca tgcagatggc ctataggttc   5640
aatggcatcg gcgtcaccca gaacgtgctg tatgaaaacc agaaactgat tgccaaccag   5700
ttcaatagcg ccatcggcaa aatccaagac agcctctcct ccacagcttc cgctctcgga   5760
aaactgcaag acgtcgtgaa ccaaaatgcc caagccctca acacactggt gaagcagctc   5820
tccagcaact ttggagctat ctccagcgtg ctgaacgata ttctgtctag actggataaa   5880
gtcgaggccg aggtgcaaat cgatagactg atcaccggca gactccagtc tctgcaaacc   5940
tatgtgaccc agcaactcat tagggccgcc gagatcagag cctccgccaa tctggccgct   6000
acaaagatga gcgagtgcgt gctgggccaa tccaagagag tggacttctg tggcaagggc   6060
```

```
tatcatctca tgagcttccc ccaatccgcc cctcatggcg tggtcttcct ccatgtgacc      6120
tacgtccccg cccaagagaa gaacttcaca acagctcccg ccatctgcca tgatggcaag      6180
gctcatttcc ccagagaagg cgtgtttgtg tccaatggca cacactggtt cgtcacccag      6240
aggaatttct atgaacccca gatcatcacc accgacaaca ccttcgtctc cggcaactgc      6300
gatgtggtca tcggcatcgt gaacaacaca gtgtatgacc ctctccaacc cgagctggac      6360
agcttcaagg aggagctcga taaatatttt aagaaccata catccccga cgtggacctc      6420 ggcgacatca gcggcattaa cgccagcgtg gtgaacatcc agaaggagat cgataggctc      6480
aacgaggtgg ccaagaatct gaacgaaagc ctcatcgatc tgcaagagct cggcaagtac      6540
gagcagtaca tcaagtggcc ttggtacatc tggctcggct ttattgccgg actgatcgct      6600
atcgtcatgg tgaccatcat gctgtgctgc atgacaagct gctgtagctg tctgaaaggc      6660
tgttgtagct gcggaagctg ctgcaagttc gatgaggacg acagcgagcc cgtgctgaag      6720
ggcgtgaagc tgcactacac atagtagtag agatctacgt atgatcagcc tcgactgtgc      6780
cttctagttg ccagccatct gttgtttgcc cctcccccgt gccttccttg accctggaag      6840
gtgccactcc cactgtcctt tcctaataaa atgaggaaat tgcatcgcat tgtctgagta      6900
ggtgtcattc tattctgggg ggtggggtgg gcaggacaca caaggggag gattgggaag      6960 acaatagcag gcatgctggg gatgcggtgg gctctatggc ttctgaggcg gaaagaacca      7020 gctgggctc gacagctcga ctctagaatt gcttcctcgc tcactgactc gctgcgctcg      7080
gtcgttcggc tgcggcgagc ggtatcagct cactcaaagg cggtaatacg gttatccaca      7140
gaatcagggg ataacgcagg aaagaacatg tgagcaaaag gccagcaaaa ggccaggaac      7200
cgtaaaaagg ccgcgttgct ggcgtttttc cataggctcc gcccccctga cgagcatcac      7260
aaaaatcgac gctcaagtca gaggtggcga aacccgacag gactataaag ataccaggcg      7320
tttccccctg gaagctccct cgtgcgctct cctgttccga ccctgccgct taccggatac      7380
ctgtccgcct ttctcccttc gggaagcgtg gcgctttctc aatgctcacg ctgtaggtat      7440
ctcagttcgg tgtaggtcgt tcgctccaag ctgggctgtg tgcacgaacc ccccgttcag      7500
cccgaccgct gcgccttatc cggtaactat cgtcttgagt ccaacccggt aagacacgac      7560
ttatcgccac tggcagcagc cactggtaac aggattagca gagcgaggta tgtaggcggt      7620
gctacagagt tcttgaagtg gtggcctaac tacggctaca ctagaaggac agtatttggt      7680
atctgcgctc tgctgaagcc agttaccttc ggaaaaagag ttggtagctc ttgatccggc      7740
aaacaaacca ccgctggtag cggtggtttt tttgtttgca agcagcagat tacgcgcaga      7800
aaaaaaggat ctcaagaaga tcctttgatc ttttctacgg ggtctgacgc tcagtggaac      7860
gaaaactcac gttaagggat tttggtcatg agattatcaa aaaggatctt cacctagatc      7920
cttttaaatt aaaaatgaag ttttaaatca atctaaagta tatatgagta aacttggtct      7980
gacagttacc aatgcttaat cagtgaggca cctatctcag cgatctgtct atttcgttca      8040
tccatagttg cctgactc                                                    8058
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

-continued

```
ttacaaacat tggccgcaaa                                            20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcgcgacatt ccgaagaa                                              18

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
acaatttccc ccagcgcttc ag                                         22
```

SAR-CoV-2 DNA VACCINE AND METHOD OF ADMINISTERING THEREOF

STATEMENT AS TO RIGHTS OR INVENTIONS MADE UNDER FEDERALLY SPONSORED RESEARCH AND DEVELOPMENT

This invention was made with government support from Defense Health Program with programmatic oversight from the Military Infectious Diseases Research Program, project number 188155773. The United States government has certain rights in the invention.

CROSS REFERENCE TO RELATED APPLICATION

This application is a National Stage of International Application No. PCT/US2021/054784, filed Oct. 13, 2021, which claims the benefit of the filing date of U.S. Provisional Patent Application No. 63/091,053, filed Oct. 13, 2020, the entire contents of each of which are incorporated herein by reference.

REFERENCE TO SEQUENCE LISTING

The instant application contains a Sequence Listing which has been submitted electronically in ASCII format and is hereby incorporated by reference in its entirety. Said ASCII copy, created on Oct. 13, 2021, is named 200563-0051-00-WO-000004_SL.txt and is 28,095 bytes in size.

BACKGROUND

The COVID-19 pandemic has necessitated the rapid development of candidate vaccines and treatments targeting the severe acute respiratory syndrome coronavirus 2 (SARS-CoV-2) virus. Infection with SARS-CoV-2 virus results in either asymptomatic infection or symptomatic disease ranging from mild to severe respiratory symptoms (Huang, C. et al., *Lancet* 2020, 395: 497-506). Many factors contributing to the spread of this virus including a large number of asymptomatic cases (Lavezzo, E. et al., *Nature* 2020, 584: 425-429) and transmission prior to the onset of symptoms (Furukawa, N. W. et al., *Emerg. Infect. Dis* 2020, 16(7): e201595). An effective vaccine would be an invaluable medical countermeasure to protect individuals, prevent transmission, and contribute to containing and ultimately ending this pandemic.

According to the World Health Organization, as of Sep. 30, 2020, there were 41 SARS-CoV-2 vaccines in clinical trials (Phases I, II and III) and 151 vaccines in preclinical development (World Health Organization, DRAFT landscape of COVID-19 vaccine candidates, 2020). Of these vaccines in preclinical development, several have been tested for immunogenicity in mice and nonhuman primates. Few have been tested in disease models such as the Syrian hamster model. The Syrian hamster has become a leading animal model for SARS-CoV-2 medical countermeasure testing, because it does not require a modified virus, or animal, and there are several similarities to human COVID-19 disease including rapid breathing, lethargy, ruffled fur and moderate (<10%) weight loss (Cohen, *J., Science* 2020, 368: 221-222 and Chan, J. F. et al., *Clin. Infect. Dis.,* 2020, 71(9): 2428-2446). Histopathology includes areas of lung consolidation, followed by pneumocyte hyperplasia as the virus is cleared. At least three candidate vaccines have been tested for efficacy using the Syrian hamster model (Felipe, L. S. et al., *bioRxiv,* 2020.2007.2008.193045; Tostanoski, L. H. et al., *Nature Medicine* 2020, 26: 1694-1700; and Yahalom-Ronen, Y. et al. *bioRxiv,* 2020.2006.2018.160655).

A Syrian hamster model of severe COVID-19 disease has been developed by using cyclophosphamide (CyP) to transiently immunosuppress the hamsters (Brocato, R. L. et al., *J. Virol.* 2020, 94(22):e01683-20). In this chemically induced animal model, lymphopenia is induced by CyP treatment starting 3 days before exposure to virus. After a relatively low dose of virus (1,000 PFU), the immunosuppressed hamsters develop a protracted disease with >15% weight loss over several days and other indicators of severe disease including high levels of virus in the lungs.

Nevertheless, testing of any SARS-CoV-2 DNA vaccine in both wild-type and transiently-immunosuppressed hamsters, using an jet injector, has not been performed.

SUMMARY

The current disclosure provides a severe acute respiratory syndrome coronavirus 2 (SARS-CoV-2) spike-based DNA composition, which can be used as a DNA vaccine to elicit neutralizing antibody production in a human subject. Also provided is a method of administering the SARS-CoV-2 spike-based DNA composition as a DNA vaccine to a human subject. Further provided is a use of the SARS-CoV-2 spike-based DNA composition for the elicitation of an immune response to a SARS-CoV-2 in a human subject.

In one aspect, the SARS-CoV-2 spike-based DNA composition may comprise a recombinant DNA construct in a plasmid, wherein the recombinant DNA construct comprises a nucleic acid sequence encoding a SARS-CoV-2 spike protein, and wherein the DNA composition, when administered to a human subject after at least two administrations, is capable of eliciting neutralizing antibody production in the human subject.

In another aspect, the SARS-CoV-2 spike protein encoded by recombinant DNA construction of the SARS-CoV-2 spike-based DNA composition may comprise SEQ ID NO: 2. Alternatively, the encoded SARS-CoV-2 spike protein may be selected from the group consisting of:

(a) the spike protein from an Alpha SARS-CoV-2 variant (B.1.1.7), which comprises the following mutations: Δ69, Δ70, D144Y, E484K, S494P, N501Y, A570D, D614G, P681H, T716I, S982A, and D1118H of SEQ ID NO: 2;

(b) the spike protein from a Beta SARS-CoV-2 variant (B.1.351), which comprises the following mutations: L18F, D80A, D215G, Δ242, Δ243, Δ244, R246I, K417N, E484K, N501Y, D614G, and A701V of SEQ ID NO: 2;

(c) the spike protein from a Gamma SARS-CoV-2 variant (P.1), which comprises the following mutations: L18F, T20N, P26S, D138Y, R190S, K417T, E484K, N501Y, D614G, H655Y, T1027I, and V1176F of SEQ ID NO: 2; and (d) the spike protein from a Delta SARS-CoV-2 variant (B.1.617.2), which comprises the following mutations: T19R, G142D, Δ156, Δ157, R158G, L452R, T478K, D614G, P681R, and D950N of SEQ ID NO: 2.

In a further aspect, the SARS-CoV-2 spike-based DNA composition may comprise a recombinant DNA construct comprising a human codon-optimized nucleic acid sequence encoding the SARS-CoV-2 spike protein. For example, the human codon-optimized nucleic acid sequence may comprise SEQ ID NO: 1.

In yet another aspect, the SARS-CoV-2 spike-based DNA composition may further comprises a pharmaceutically acceptable carrier, stabilizer, and/or excipient. Additionally or alternatively, the SARS-CoV-2 spike-based DNA composition may further comprise an adjuvant. The adjuvant typically may be a liposome-based adjuvant; a lipid nanoparticle (LNP); a saponin-based adjuvant made of nanometer particles, cholesterol, and phospholipid; or an oil-and-water emulsion with or without saponin.

Also provided is a method of eliciting an immune response to a SARS-CoV-2 in a human subject, wherein the method may comprise administering to the human subject an effective amount of the SARS-CoV-2 spike-based DNA composition. About 5.0 mg of the plasmid may be administered to the human subject without any adjuvant, or about 0.5 mg of the plasmid may be administered with an adjuvant, to eliciting the immune response to a SARS-CoV-2 in a human subject.

In one aspect, the SARS-CoV-2 spike-based DNA composition may be administered to the human subject intramuscularly, subcutaneously, or intradermally to eliciting an immune response. Typically, the SARS-CoV-2 spike-based DNA composition may be administered to the human subject intramuscularly using a jet injector.

In another aspect, the SARS-CoV-2 spike-based DNA composition may be administered at least twice to the human subject. Additionally, the SARS-CoV-2 spike-based DNA composition maybe administered to the human subject at least twice, wherein each administration may be separated by at least four weeks.

In a further aspect, SARS-CoV-2 spike-based DNA composition may be administered as a booster shot. For example, the human subject administered with the booster shot previously was administered with a SARS-CoV-2 spike-based DNA that may differ from the SARS-CoV-2 spike-based DNA in the booster shot. Alternatively, the booster shot may be administered to the human subject who previously was administered a SARS-CoV-2 mRNA vaccine, a SARS-CoV-2 adenovirus vaccine, or a SARS-CoV-2 protein vaccine.

BRIEF DESCRIPTION OF THE DRAWINGS

FIG. 1A illustrates experimental design. Groups of 8 hamsters each were vaccinated (vacc) with the nCoV-S(JET) DNA vaccine, 1×PBS (negative control), or a MERS-CoV DNA vaccine (a coronavirus vaccine) and then challenged with 100,000 PFU of SARS-CoV-2 virus by the intranasal route. FIG. 1B depicts PRNT80 titers from serum collected at indicated timepoints after 1 (open symbols) and 2 (closed symbols) vaccinations (LLOQ=20, grey shade). FIG. 1C depicts average animal weights relative to starting weight. Viral RNA was quantified in pharyngeal swabs (FIG. 1D) and lung homogenates (FIG. 1E) respectively (LLOQ=50 copies, grey shade). FIG. 1F depicts infectious virus as measured by plaque assay (LLOD=50 PFU, grey shade). FIGS. 1G-1I illustrate bright field imagery of H&E slides of lungs respectively from nCoV-S(JET) DNA (FIG. 1G), PBS (FIG. 1H), or MERS-CoV (FIG. 1I) vaccinated hamsters. FIGS. 1J-1L depict ISH slides to detect SARS-CoV-2 genomic RNA depicted in lung sections respectively of nCoV-S(JET) DNA (FIG. 1J), 1×PBS (FIG. 1K), and MERS-CoV (FIG. 1L) vaccinated hamsters. Rare, positive labeling in nCoV-S(JET) DNA vaccinated hamster lung sections were detected (arrows). Asterisks indicate that results were statistically significant, as follows: *, P<0.05; , P<0.01; *, P<0.001; ns, not significant. Scale bars=400 microns.

FIG. 2A illustrates experimental design. Groups of 8 hamsters each were vaccinated (vacc) with the nCoV-S(JET) DNA vaccine or PBS, immunosuppressed with cyclophosphamide, and then challenged with 1,000 PFU of SARS-CoV-2 virus by the intranasal route. FIG. 2B depicts PRNT80 and PsVNA80 titers from serum collected at indicated timepoints after 1 (open symbols) and 2 (closed symbols) vaccinations (LLOQ=20, grey shade). Lymphopenia was confirmed by hematology (FIG. 2C). FIG. 2D depicts average animal weights relative to starting weight. Viral RNA was quantified in pharyngeal swabs (FIG. 2E) and lung homogenates (FIG. 2F) respectively (LLOQ=50 copies, grey shade). FIG. 2G depicts infectious virus as measured by plaque assay (LLOD=50 PFU, grey shade). A single animal from the PBS group succumbed on Day 9 post-exposure (open symbol in FIG. 2F and FIG. 2G). FIGS. 2H and 2I depict bright field imagery of H&E slides of lungs from nCoV-S(JET) DNA (FIG. 2H) or PBS (FIG. 2I) vaccinated hamsters. FIGS. 2J and 2K depict ISH slides to detect SARS-CoV-2 genomic RNA in lung sections of nCoV-S(JET) DNA (FIG. 2J) and PBS (FIG. 2K) vaccinated hamsters. Rare, positive labeling in nCoV-S(JET) DNA vaccinated hamster lung sections were detected (arrows). Asterisks indicate that results were statistically significant, as follows: *, P<0.05; , P<0.01; *, P<0.001; ns, not significant. Scale bars=400 microns.

FIGS. 3A-3B depict expression of pWRG/nCoV-S(opt) plasmid in 293T cells. Expression of the coronavirus' spike protein was confirmed by transfection of 293T cells followed by immunofluorescence antibody test (IFAT) using human convalescent plasma (FIG. 3A) and compared to empty vector (FIG. 3B).

DETAILED DESCRIPTION

Figure 1A:
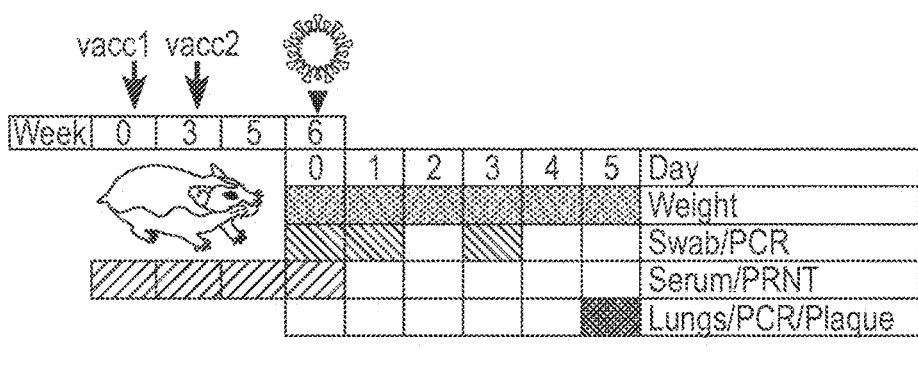
FIGS. 1A-1L depict evaluation of a nCoV-S(JET) DNA vaccine in Syrian hamsters.

Provided are compositions and methods that are useful to elicit an immune response to a SARS-CoV-2 in human subjects.

Definitions

As used in the specification and embodiments, the singular forms "a," "an" and "the" include plural references unless the context clearly dictates otherwise. For example, the term "a cell" includes a plurality of cells, including mixtures thereof. Similarly, use of "a compound" for treatment or preparation of medicaments as described herein contemplates using one or more compounds of this invention for such treatment or preparation unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The term "about" in relation to a reference numerical value, and its grammatical equivalents as used herein, can include the reference numerical value itself and a range of values plus or minus 10% from that reference numerical value. For example, the term "about 10" includes 10 and any amounts from and including 9 to 11. In some cases, the term "about" in relation to a reference numerical value can also include a range of values plus or minus 10%, 9%, 8%, 7%, 6%, 5%, 4%, 3%, 2%, or 1% from that reference numerical value. In some embodiments, "about" in connection with a number or range measured by a particular method indicates that the given numerical value includes values determined by the variability of that method.

The "percentage identity" between polypeptide sequences can be calculated using commercially available algorithms that compare a reference sequence with a query sequence. In some embodiments, polypeptides are 70%, at least 70%, 75%, at least 75%, 80%, at least 80%, 85%, at least 85%, 90%, at least 90%, 92%, at least 92%, 95%, at least 95%, 97%, at least 97%, 98%, at least 98%, 99%, or at least 99% or 100% identical to a reference polypeptide, or a fragment thereof (e.g., as measured by BLASTP or CLUSTAL, or other polypeptide alignment software) using default parameters. Similarly, nucleic acids can also be described with reference to a starting nucleic acid, e.g., they can be 50%, at least 50%, 60%, at least 60%, 70%, at least 70%, 75%, at least 75%, 80%, at least 80%, 85%, at least 85%, 90%, at least 90%, 95%, at least 95%, 97%, at least 97%, 98%, at least 98%, 99%, at least 99%, or 100% identical to a reference nucleic acid or a fragment thereof (e.g., as measured by BLASTN or CLUSTAL, or other nucleic acid alignment software using default parameters). When one molecule is said to have a certain percentage of sequence identity with a larger molecule, it means that when the two molecules are optimally aligned, the percentage of residues in the smaller molecule finds a match residue in the larger molecule in accordance with the order by which the two molecules are optimally aligned, and the "%" (percent) identity is calculated in accord with the length of the smaller molecule.

The terms "coding sequence" or "coding region" and the corresponding abbreviation "cds" as used herein will be recognized and understood by the person of ordinary skill in the art, and are, e.g., intended to refer to a sequence of several nucleotide triplets, which may be translated into a peptide or protein. A coding sequence in the context of the present compositions may be a nucleic acid sequence such as a DNA sequence, preferably an RNA sequence, consisting of a number of nucleotides that may be divided by three, which starts with a start codon and which preferably terminates with a stop codon.

The term "immune response" will be recognized and understood by the person of ordinary skill in the art, and is, e.g., intended to refer to a specific reaction of the adaptive immune system to a particular antigen (so called specific or adaptive immune response) or an unspecific reaction of the innate immune system (so called unspecific or innate immune response), or a combination thereof.

By "codon optimized" is meant to modify a coding nucleic sequence to include codons that are optimized for expression in a designated host organism. Redundancy in the genetic code allows some amino acids to be encoded by more than one codon, but certain codons are less "optimal" than others because of the relative availability of matching tRNAs as well as other factors. Codon optimized sequences can be synthetic sequences, and encode the identical polypeptide encoded by the non-codon optimized parent polynucleotide. Preferably the nucleic acid described herein is codon optimized for use in humans or primates.

The term "immune system" will be recognized and understood by the person of ordinary skill in the art, and is, e.g., intended to refer to a system of the organism that may protect the organisms from infection. If a pathogen succeeds in passing a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts typically contains so called humoral and cellular components.

By "effective amount," in the context of modulating an immune response or treating or preventing a disease or condition, is meant the administration of that amount of composition to an individual in need thereof, either in a single dose or as part of a series, that is effective for achieving that modulation, treatment or prevention. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

It will be understood that "eliciting" or "inducing" an immune response as contemplated herein includes stimulating a new immune response and/or enhancing a previously existing immune response.

An "immune response" or "immunological response" refers to the concerted action of any one or more of lymphocytes, antigen-presenting cells (APCs), phagocytic cells, granulocytes, and soluble macromolecules produced by the above cells or the liver (e.g., antibodies, cytokines, and complement) that results in selective damage to, destruction of, or elimination from the body of invading pathogens, or cells or tissues infected with the pathogens. In some embodiments, an "immune response" encompasses the development in an individual of a humoral and/or a cellular immune response to a polypeptide that is encoded by an introduced synthetic coding sequence of the invention. As known in the art, the terms "humoral immune response" includes and encompasses an immune response mediated by antibody molecules, while a "cellular immune response" includes and encompasses an immune response mediated by T-lymphocytes and/or other white blood cells. Hence, an immunological response may include one or more of the following effects: the production of antibodies by B-cells; and/or the activation of suppressor T-cells; and/or memory/effector T-cells directed specifically to an antigen or antigens present in the composition or vaccine of interest. In some embodiments, these responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art (e.g., Montefiori et al., *J. Clin. Microbiol.* 1988, 26: 231-235; and Dreyer et al., *AIDS Res. Hum. Retroviruses* 1999, 15(17): 1563-1571). The innate immune system of mammals also recognizes and responds to molecular features of pathogenic organisms and cancer cells via activation of Toll-like receptors and similar receptor molecules on immune cells. Upon activation of the innate immune system, various non-adaptive immune response cells are activated to, e.g., produce various cytokines, lymphokines, and chemokines. Cells activated by the innate immune response system include immature and mature dendritic cells of, for example, the monocyte and plasmacytoid lineage (MDC, PDC), as well as gamma, delta, alpha, and beta T cells and B cells and the like. Thus, the present invention also contemplates an immune response wherein the immune response involves both an innate and adaptive response.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are known in the art.

The term "pharmaceutically acceptable carrier" or "pharmaceutically acceptable excipient" as used herein preferably includes the liquid or non-liquid basis of the composition for administration. If the composition is provided in liquid form, the carrier may be water, e.g., pyrogen-free water; isotonic saline or buffered (aqueous) solutions, e.g., phosphate, citrate, etc. buffered solutions. Water or preferably a buffer, more preferably an aqueous buffer, may be used, containing a sodium salt, preferably at least 50 mM of a sodium salt; a calcium salt, preferably at least 0.01 mM of a calcium salt; and optionally a potassium salt, preferably at least 3 mM of a potassium salt. According to preferred embodiments, the sodium, calcium and, optionally, potassium salts may occur in the form of their halogenides, e.g., chlorides, iodides, or bromides, in the form of their hydroxides, carbonates, hydrogen carbonates, or sulfates, etc. Examples of sodium salts include NaCl, NaI, NaBr, $Na_2CO_3$, $NaHCO_3$, $Na_2SO_4$; examples of the optional potassium salts include KCl, KI, KBr, $K_2CO_3$, $KHCO_3$, $K_2SO_4$; and examples of calcium salts include $CaCl_2$, $CaI_2$, $CaBr_2$, $CaCO_3$, $CaSO_4$, $Ca(OH)_2$.

The term "nucleic acid" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

The term "adjuvant" as used herein will be recognized and understood by the person of ordinary skill in the art, and is for example intended to refer to a pharmacological and/or immunological agent that may modify, e.g. enhance, the effect of other agents or that may be suitable to support administration and delivery of the composition. The term "adjuvant" refers to a broad spectrum of substances. Typically, these substances are able to increase the immunogenicity of antigens. For example, adjuvants may be recognized by the innate immune systems and, e.g., may elicit an innate immune response (that is, a non-specific immune response). "Adjuvants" typically do not elicit an adaptive immune response. In the context of the invention, adjuvants may enhance the effect of the antigenic peptide or protein provided by the nucleic acid. In that context, the at least one adjuvant may be selected from any adjuvant known to a skilled person and suitable for the present case, i.e. supporting the induction of an immune response in a subject, e.g. in a human subject.

As used herein, the terms "encode," "encoding," and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode," "encoding," and the like include an RNA product resulting from transcription of a DNA molecule, a protein resulting from translation of an RNA molecule, a protein resulting from transcription of a DNA molecule to form an RNA product and the subsequent translation of the RNA product, or a protein resulting from transcription of a DNA molecule to provide an RNA product, processing of the RNA product to provide a processed RNA product (e.g., mRNA) and the subsequent translation of the processed RNA product.

By "administration", "administer" and "administering" is meant the introduction into a subject of a vaccine composition. The vaccine composition is to be administered at least two times. By administered at least two times, if the subject is human, there is to be a span of preferably at least 3 weeks, at least 4 weeks, or at least 8 weeks between the at least two administrations. If the administration is in the form of a booster administer, the booster administration to the subject is given for example at least about 3 months, at least about 4 months, at least about 5 months, at least about 6 months, at least about 7 months, at least about 8 months, at least about 9 months, at least about 10 months, at least about 11 months at least about 12 months (one year), at least about 18 months after the second of the at least two administrations.

DNA Vaccine

Provided herein are immunogenic compositions, such as DNA vaccine compositions, comprising a recombinant nucleic acid in a vector, e.g., a plasmid. The recombinant nucleic acid encodes a SARS-CoV-2 spike protein. The SARS-CoV-2 spike protein may be the one having the amino acid sequence of SEQ ID NO: 2, corresponding to the Wuhan coronavirus 2019 nCoV S protein (Genbank accession QHD43416). Alternatively, the encoded SARS-CoV-2 spike protein may have an amino acid sequence identity of at least 90%, at least 91%, at least 92%, at least 93%, at least 94%, at least 95%, at least 96%, at least 97%, at least 98%, at least 99%, or at least 99.5% to SEQ ID NO: 2. For example, the SARS-CoV-2 spike protein encoded by the recombinant DNA can be one selected from the group consisting of:

(a) the spike protein from an Alpha coronavirus variant (B.1.1.7), which comprises the following mutations: Δ69, Δ70, D144Y, E484K, S494P, N501Y, A570D, D614G, P681H, T716I, S982A, and D1118H of SEQ ID NO: 2;

(b) the spike protein from a Beta coronavirus variant (B.1.351), which comprises the following mutations: L18F, D80A, D215G, Δ242, Δ243, Δ244, R246I, K417N, E484K, N501Y, D614G, and A701V of SEQ ID NO: 2;

(c) the spike protein from a Gamma coronavirus variant (P.1), which comprises the following mutations: L18F, T20N, P26S, D138Y, R190S, K417T, E484K, N501Y, D614G, H655Y, T1027I, and V1176F of SEQ ID NO: 2; and (d) the spike protein from a Delta coronavirus variant (B.1.617.2), which comprises the following mutations: T19R, G142D, Δ156, Δ157, R158G, L452R, T478K, D614G, P681R, and D950N of SEQ ID NO: 2.

The DNA vaccine composition may further comprises a pharmaceutically acceptable carrier, stabilizer, and/or excipient.

The choice of a pharmaceutically acceptable carrier as defined herein is determined, in principle, by the manner, in which the pharmaceutical composition(s) or vaccine according to the invention is administered.

The DNA vaccine of described herein may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freund's incomplete adjuvant, a lipopolysaccharide (LPS) analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents. A transfection facilitating agent can include a polyanion, polycation, including poly-L-glutamate (LGS), or a lipid. If the transfection facilitating agent is poly-L-glutamate, then the poly-L-glutamate may be present in the vaccine at a concentration less than 6 mg/ml. The transfection facilitating agent may also include surface active agents such as immune-stimulating complexes (ISCOMS), Freund's incomplete adjuvant, LPS analog including monophosphoryl lipid A, muramyl peptides, quinone analogs, and vesicles such as squalene and squalene, and hyaluronic acid may also be used administered in conjunction with the genetic construct. The DNA vaccines may also include a transfection facilitating agent such as lipids, liposomes, including lecithin liposomes or other liposomes known in the art, as a DNA-liposome mixture (e.g., WO9324640), calcium ions, viral proteins, polyanions, polycations, or nanoparticles, or other known transfection facilitating agents. Concentration of the transfection agent in the vaccine can be less than about 4 mg/ml, less than about 2 mg/ml, less than about 1 mg/ml, less than about 0.750 mg/ml, less than about 0.500 mg/ml, less than about 0.250 mg/ml, less than about 0.100 mg/ml, less than about 0.050 mg/ml, or less than about 0.010 mg/ml.

The DNA vaccine composition described herein may contains one or more adjuvants. The adjuvant may be a liposome-based adjuvant; a lipid nanoparticle (LNP); a saponin-based adjuvant made of nanometer particles, cholesterol, and phospholipid; or an oil-and-water emulsion with or without saponin. Typical liposome-based adjuvants include those described in Alving, C. R. et al., *Expert Rev. Vaccines* 2020, 19(3): 279-292 (e.g, WO2015147899 and WO2015148648 which are incorporated herein for all purposes). Lipid nanoparticle (LNP) adjuvants typically comprise ionizable cationic lipid, non-cationic lipid, sterol, and PEG lipid components along with the nucleic acid cargo of interest. Methods of generating lipid nanoparticle (LNP) adjuvants are generally well known in the art (e.g., WO2021159130 and US 2017/0210697 which are incorporated herein for all purposes). A typical saponin-based adjuvant made of nanometer particles, cholesterol, and phospholipid is Matrix-M™ by Novavax. A typical oil-in-water adjuvant is MF59®, which comprises an oil-in-water emulsion of squalene oil (see, e.g., O'Hagan, D. T. et al., *Expert Review of Vaccines* 2014, 10(4):447-462).

Method of Administering the DNA Vaccine

The DNA vaccine described herein can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The vaccine can be administered prophylactically or therapeutically. In prophylactic administration, the vaccines can be administered in an amount sufficient to induce an immune response. In therapeutic applications, the vaccines are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the subject, and the judgment of the prescribing physician.

The DNA vaccine described herein can be delivered via a variety of routes. Typical delivery routes include parenteral administration, e.g., intradermal, intramuscular or subcutaneous delivery. Other routes include oral administration, intranasal, and intravaginal routes. The vaccine can also be administered to muscle (intramuscular or i.m. injection), or can be administered via intradermal (intradermally) or subcutaneous (s.c. or subcutaneously) injections, or transdermally, such as by iontophoresis. Epidermal administration of the vaccine can also be employed. Epidermal administration can involve mechanically or chemically irritating the outermost layer of epidermis to stimulate an immune response to the irritant.

The DNA vaccine can be administered via injection, via jet injector (which forces a liquid into the skin under pressure), or via particle bombardment, in which the DNA may be coated onto particles of sufficient density to penetrate the epithelium. Projection of these particles into the skin results in direct transfection of both epidermal cells and epidermal Langerhans cells. Langerhans cells are antigen presenting cells (APCs) which take up the DNA, express the encoded peptides, and process these for display on cell surface MHC proteins. Transfected Langerhans cells migrate to the lymph nodes where they present the displayed antigen fragments to lymphocytes, invoking an immune response.

Using a jet injector, the DNA vaccine is delivered via a high-speed jet of liquid that painlessly pierces the tissue. Such needle-free injectors are well suited to deliver vaccines to all types of tissues, particularly to skin and mucosa. In some embodiments, a needle-free injector may be used to propel a liquid that contains the DNA vaccine to the surface and into the human subject's skin or mucosa.

The DNA vaccine described herein can be administered about 1.0 mg, about 2.0 mg, about 3.0 mg, about 4.0 mg, about 5.0 mg, about 6.0 mg, about 7.0 mg, about 8.0 mg, about 9.0 mg, or about 10.0 mg of plasmid DNA to an human subject if no adjuvant is administered. Alternatively, the DNA vaccine described herein may be administered in an amount of about 0.1 mg, about 0.2 mg, about 0.3 mg, about 0.4 mg, about 0.5 mg, about 0.6 mg, about 0.7 mg, about 0.8 mg, about 0.9 mg, or about 1.0 mg of plasmid DNA to a human subject if at least one adjuvant is administered. The DNA vaccine described herein may be administered to a human subject at least twice or at least three times, for example, to elicit a more robust immune response. Multiple administrations of the DNA vaccine described herein may be separated by at least three weeks, at least four weeks, or at least eight weeks. The DNA vaccine described herein may be administered as a booster shot to a human subject who was administered a different SARS-CoV-2 vaccine, for example, a DNA vaccine comprising a different SARS-CoV-2 spike-based DNA, a SARS-CoV-2 mRNA vaccine, a SARS-CoV-2 adenovirus vaccine, and/or a SARS-CoV-2 protein vaccine. A booster may be given 6 months, 9 months, 12 months, or 18 months after the prior vaccine administration. Typically, a booster can be administered if a neutralizing antibody response by the prior vaccination is found to be below a certain threshold.

EXAMPLES

Materials and Methods
Ethics

Animal research was conducted under an IACUC approved protocol at USAMRIID (USDA Registration Number 51-F-00211728 & OLAW Assurance Number A3473-01).
Plasmid Construction For both pWRG/nCoV-S(opt) and pWRG/MERS-S(opt), the full-length coronavirus S gene open reading frame (ORF), preceded at the N-terminus by a Kozak sequence (ggcacc) (SEQ ID NO: 3), was human codon usage-optimized and synthesized by Genewiz (South Plainfield, NJ) and cloned into the BglII-NotI site of the DNA vaccine vector pWRG. The SARS-nCoV-2 S sequence used was the Wuhan coronavirus 2019 nCoV S gene open reading frame (Genbank accession QHD43416). The MERS sequence used was the nc Jordan-N3/2012 S gene open reading frame (Genbank accession AGH58717.1). The plasmids for use in vaccinations were produced commercially and diluted in 1× phosphate buffered saline (PBS) to 2 mg/mL (Aldevron, Fargo ND). Expression of the spike protein from pWRG/nCoV-S(opt) was confirmed by transfection of 293T cells followed by an immunofluorescence antibody test (IFAT) using heat inactivated (56° C., 30 min) human convalescent plasma NRS-53265 (ATCC, Manassa, VA) and compared to empty vector transfected 293T cells (FIGS. 3A-3B).

A second plasmid for the PsVNA was constructed by deleting the 21 amino acids from the carboxy terminus of the full length plasmid, pWRG/cOV-S(opt)Δ21 for better incorporation in to pseudovirions (Case, J. B. et al., *Cell Host Microbe* 2020 28: 475-485 e475). The pWRG/nCov-S(opt) plasmid is also called nCoV-S(JET) when combined with jet injection. The DNA sequence of pWRG/nCov-S(opt) plasmid is shown as SEQ ID NO: 4.
Animal Vaccinations Wild type (females only, aged 6-8 weeks) hamsters (*Mesocricetus auratus*) were anesthetized by inhalation of vaporized isoflurane using an IMPAC6 veterinary anesthesia machine. Fur over the semitendinosus and biceps femoris muscles (right leg) was removed using electric clippers. The PharmaJet® Tropis device was used to deliver 0.2 mg of DNA in a 0.1 mL volume intramuscularly to each animal (Brocato, R. L. et al., *J. Virol.* 2020, 94(22): e01683-20). Specifically, the disposable syringe of the device was pressed against the skin, and the device was activated resulting in the delivery of a liquid jet into the muscle and overlying tissues.
Other Animal Procedures In addition to vaccination, the following procedures were conducted after anesthetizing the hamsters as described above: intranasal challenge of virus, cyclophosphamide (CyP) intraperitoneal injections, pharyngeal swabs, and nonterminal blood collection. Intranasal instillation of SARS-CoV-2 was administered in a volume of 50 μl for the challenge doses of 1,000 PFU, and 100 μl for the challenge dose of 100,000 PFU (plaque forming units). CyP treatment (Baxter, pharmaceutical grade) consisted of an initial loading dose of 140 mg/kg, followed by maintenance doses of 100 mg/kg (e.g., as described in Brocato, R. L. et al., *J. Virol.* 2014, 88(2):811-9). Pharyngeal swabs taken from the animals were placed in 0.5 ml of complete media (Eagle's minimal essential medium (EMEM) plus 10% heat inactivated fetal bovine serum, 1% penicillin/streptomycin, 0.1% gentamycin, and 0.2% fungizone) and were used for virus detection to monitor infection and disease course in hamsters. Vena cava blood collection was limited to 7% of total blood volume per week. Terminal blood collection was performed by cardiac injection at the time of euthanasia. All work involving infected animals was performed in an animal biosafety level 3 (ABSL-3) laboratory.

SARS-CoV-2 Stock

An aliquot of the third passage of SARS-CoV-2 USA-WA-1/2020 was received from the Centers for Disease Control (CDC) and propagated in ATCC Vero 76 cells (until the cells were 99% confluent) in EMEM media containing 1% GlutaMAX, 1% NEAA (non-essential amino acid), and 10% heat-inactivated fetal bovine serum at an MOI (multiplicity of infection) of 0.01. Supernatant was collected from cell cultures exhibiting characteristic CPE (cytopathic effects) and clarified by centrifugation (10,000 g×10 minutes). Clarified virus was subjected to the following assays: identification by SARS-CoV-2 RT-PCR assay, quantification by agarose-based plaque assay, free from contaminants by growth on chocolate containing agar plates, endotoxin testing using Endosafe® nexgen-PTS, and *Mycoplasma* using a MycoAlert test kit (Lonza), and genomic sequencing. For experiments with a challenge dose of <10,000 PFU, virus passage 5 was used; for experiments with a challenge dose of 100,000 PFU, passage 6 was used. Genomic analysis indicates no changes between passage 3, 5, and 6 lots.

Viral RNA Assay

Following 3 freeze/thaws of frozen swabs in media, 250 µl of media was removed and added to 750 µl of Trizol LS. Approximately 200 mg of organ tissue was homogenized in 1.0 ml of Trizol using M tubes on the gentleMACS™ dissociator system on the RNA setting. RNA was extracted from Trizol LS or Trizol per manufacturer's protocol. A Nanodrop 8000 was used to determine RNA concentration, which was then raised to 100 ng/µl in UltraPure distilled water. Samples were run in duplicate on a BioRad CFX thermal cycler using TaqPath 1-step RT-qPCR master mix according to the CDC's recommended protocol of 25° C. for 2 minutes, 50° C. for 15 minutes, 95° C. for 2 minutes, followed by 45 cycles of, 95° C. for 3 seconds and 55° C. for 30 seconds. The forward and reverse primer and probe sequences are: 2019-nCoV_N2-F, 5'-TTA CAA ACA TTG GCC GCA AA-3' (SEQ ID NO: 5), 2019-nCoV_N2-R, 5'-GCG CGA CAT TCC GAA GAA-3' (SEQ ID NO: 6), and 2019-nCoV_N2-P, 5'-ACA ATT TCC CCC AGC GCT TCA G-3' (SEQ ID NO: 7). The limit of detection for this assay is 50 copies.

Plaque Reduction Neutralization Test (PRNT)

An equal volume of complete media (EMEM containing 10% heat-inactivated FBS, 1% Pen/Strep, 0.1% Gentamycin, 0.2% Fungizone, cEMEM) containing SARS-CoV-2 was combined with 2-fold serial dilutions of cEMEM containing antibody and incubated at 37° C. in a 5% $CO_2$ incubator for 1 hour (total volume 222 µl). 180 µl per well of the combined virus/antibody mixture was then added to 6-well plates containing 3-day old, ATCC Vero 76 monolayers and allowed to adsorb for 1 hour in a 37° C., 5% $CO_2$ incubator. 3 mL per well of agarose overlay (0.6% SeaKem ME agarose, EBME with HEPES, 10% heat-inactivated FBS, 100×NEAA, 1% Pen/Strep, 0.1% Gentamycin, and 0.2% Fungizone) was then added and allowed to solidify at room temperature. The plates were placed in a 37° C., 5% $CO_2$ incubator for 2 days, and then 2 mL per well of agarose overlay containing 5% neutral red and 5% heat-inactivated FBS is added. After one additional day in a 37° C., 5% $CO_2$ incubator, plaques were visualized and counted on a light box. PRNT80 titers are the reciprocal of the highest dilution that results in an 80% reduction in the number of plaques relative to the number of plaques visualized in the cEMEM alone (no antibody) wells.

Pseudovirion Neutralization Assay (PsVNA)

The PsVNA used to detect neutralizing antibodies in sera utilized a non-replicating vesicular stomatitis (VSV)-based luciferase expressing system described previously (Kwilas, S. et al., *Curr. Gene Ther.* 2014, 14: 200-210). For the MERS PsVNA there were no modifications, for SARS-CoV-2 assays there were two modifications: (1) no complement was used to parallel the SARS-CoV-2 PRNT assay, and (2) a monoclonal anti-VSV-G (IE9F9) was added at 100 ng/ml to eliminate any residual VSV activity in the pseudotype preparation.

Pseudovirion Production

Pseudovirions were produced using the pWRG/cOV-S (opt)Δ21 or MERS-CoV plasmid described above. HEK293T cells were seeded in T75 tissue culture flasks to be ~80% confluent the following day and were transfected with the plasmid of interest using Fugene 6 (Promega). After ~18 h the transfection media was removed and the cells were infected with VSVΔG*rLuc at a multiplicity of infection of ~0.07 for 1 h at 37° C. The media was removed and fresh media was added, the flasks were then incubated at 32° C. for 72 hours. The supernatant from infected cells was collected and clarified by high speed centrifugation, followed by a PEG 8,000 precipitation with 3.2% salt. The PEG mixture is spun at 10K×g for 45 min. The pellet was resuspended overnight in 1 mL THE buffer, then filtered using a 0.45 µm filter, aliquoted and stored at –70° C.

Plaque Assay

Approximately 200 mg of lung tissue taken and was homogenized in 1.0 mL of cEMEM using a gentleMACS M tubes and a gentleMACS™ dissociator on the RNA setting. Tubes were centrifuged to pellet debris and supernatants collected. Ten-fold dilutions of the samples were adsorbed to Vero 76 monolayers (200 µl of each dilution per well). Following a 1 hour adsorption in a 37° C., 5% $CO_2$ incubator, cells were overlaid and stained identically as described for PRNT. The limit of detection for this assay is 50 plaque forming units (PFU).

Hematology

Whole blood collected in EDTA tubes was analyzed on an HM5 hematology analyzer on the DOG2 setting.

Preparation of Tissues for Histology

Tissues were fixed in 10% neutral buffered formalin, trimmed, processed, embedded in paraffin, cut at 5 to 6 µm, and stained with hematoxylin and eosin (H&E).

Bright Field Imagery

Photographs of the H&E stained slides were taken with a Canon EOS 7D Mark II (mfr #9128B002AA) and Canon EF 100 mm f/2.8 L Macro (mfr #3554B002) lens. Slides were placed on a lightbox and photographed at 1:1 magnification with a shutter speed of 1/100 sec, aperture of f8.0, ISO 400 and saved as Canon RAW files. Contrast was adjusted equally for all images with Photoshop Lightroom and then exported as PNG files.

In Situ Hybridization

To detect SARS-CoV-2 genomic RNA in FFPE tissues, in situ hybridization (ISH) was performed using the RNAscope 2.5 HD RED kit (Advanced Cell Diagnostics, Newark, CA, USA) as described previously (Liu, J. et al., *JCI Insight* 2020, 5(12): e139042). Briefly, 40 ZZ ISH probes targeting SARS-CoV-2 genomic RNA fragment 21571-25392 (Gen- Bank #LC528233.1) were designed and synthesized by Advanced Cell Diagnostics (#854841). Tissue sections were de-paraffinized with xylene, underwent a series of ethanol washes and peroxidase blocking, and were then heated in kit-provided antigen retrieval buffer and digested by kit-provided proteinase. Sections were exposed to ISH target probe pairs and incubated at 40° C. in a hybridization oven for 2 hours. After rinsing, ISH signal was amplified using kit-provided Pre-amplifier and Amplifier conjugated to alkaline phosphatase and incubated with a Fast Red substrate solution for 10 min at room temperature. Sections were then stained with hematoxylin, air-dried, and cover slipped.

Statistical Analyses

Statistical analyses were completed using GraphPad Prism 8. Weight data was analyzed using a one-way ANOVA with multiple comparisons for experiments with ≥2 groups; unpaired t-tests were used to analyze weight data for experiments with 2 groups. Comparisons of lymphocyte levels and lung viral load was assessed using a one-way ANOVA with multiple comparisons for experiments with ≥2 groups; unpaired t-tests were used to analyze weight data for experiments with 2 groups. Significance of survival data was assessed using log-rank tests. In all analyses, P<0.05 is considered statistically significant.

Figure 1B:
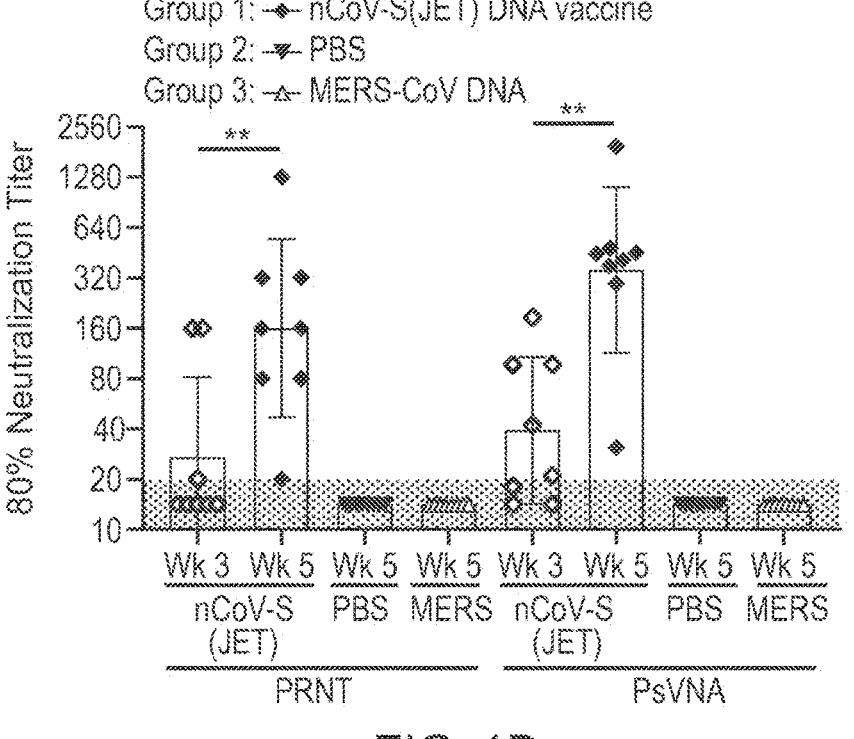
Figure 4A:
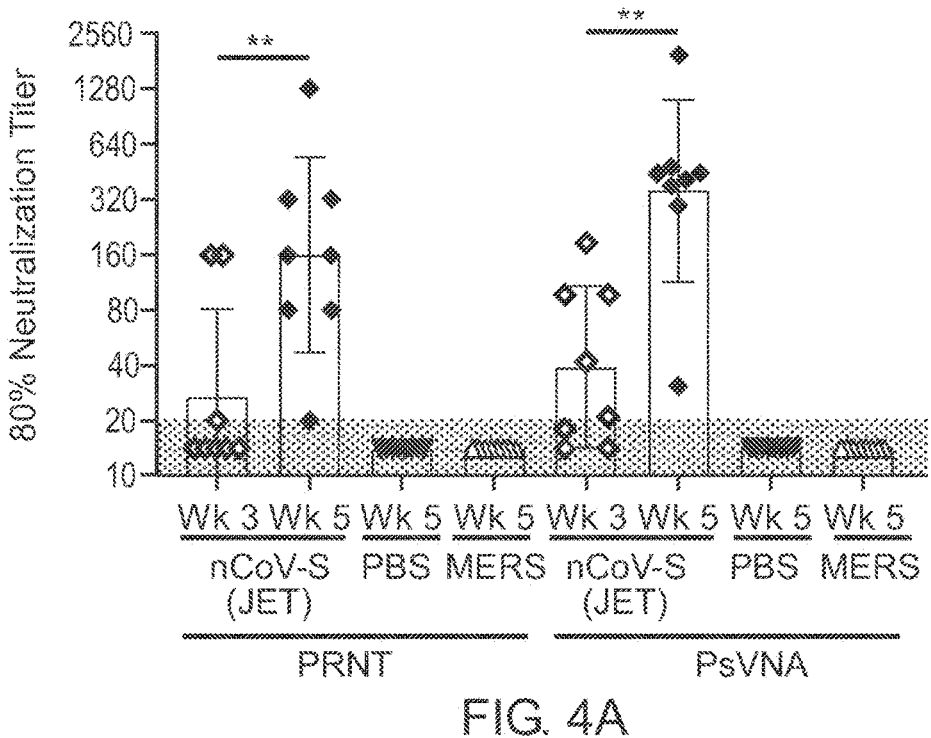
FIGS. 4A-4B depict neutralization titers of hamsters vaccinated with nCoV-S(JET) DNA vaccine. Eighty percent neutralization titers by PRNT and PsVNA of hamsters shown in FIGS. 1B and 2B are plotted.
Figure 4B:
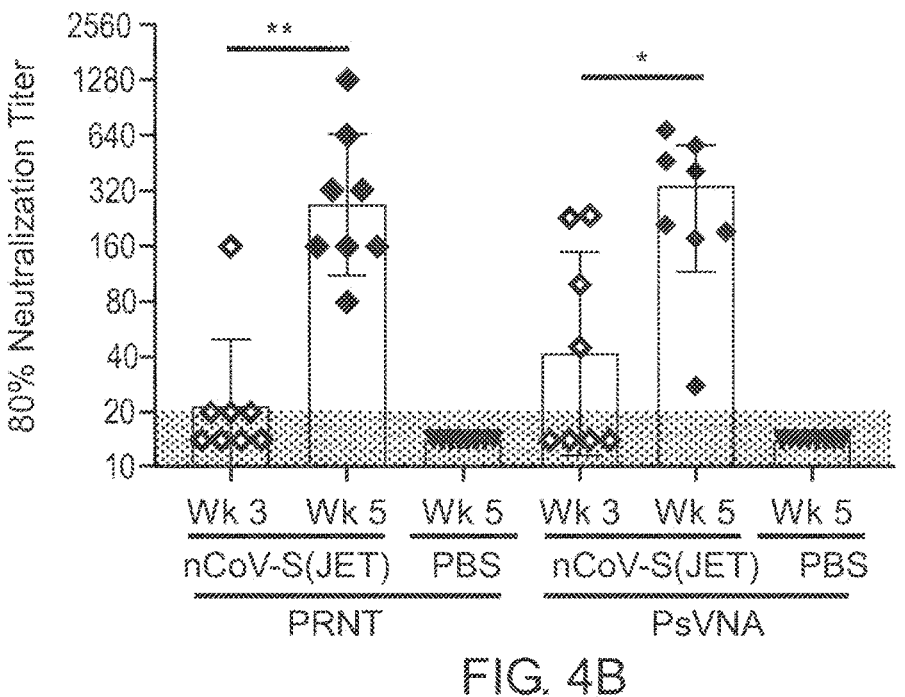
Figure 5A:
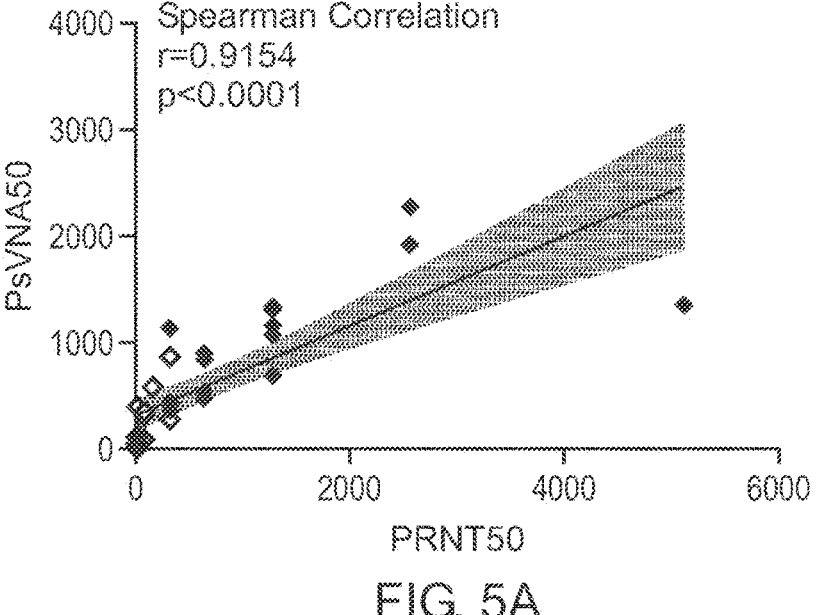
FIGS. 5A-5B depict correlation of PRNT and PsVNA assays. Fifty percent neutralization titers (FIG. 5A) and 80 percent neutralization titers (FIG. 5B) by PRNT and PsVNA from hamsters vaccinated once (open symbols) or twice (closed symbols) with the nCoV-S(JET) vaccine are plotted (positive by at least one assay only). Correlation was analyzed by Spearman with an a) r=0.9154 and P<0.0001, and b) r=0.8152 and P<0.0001 with linear regression (black line) and 95% confidence intervals (shaded area) shown.
Figure 5B:
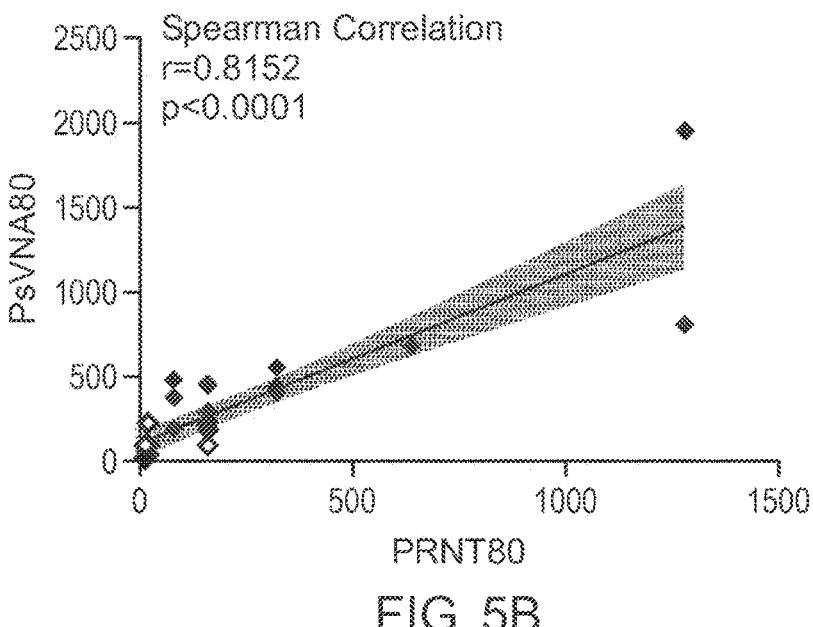
Figure 6:
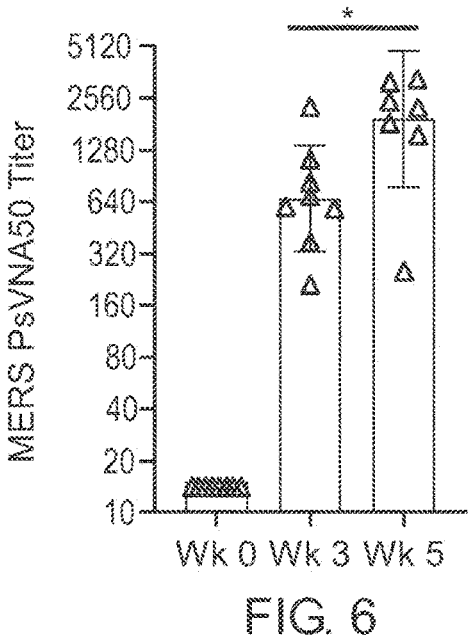
FIG. 6 depicts neutralization titers of hamsters vaccinated with MERS-CoV DNA vaccine. Eight hamsters were vaccinated with MERS-CoV DNA vaccine using Tropis. Serum collected prior to and after 1 and 2 vaccinations was analyzed by MERS PsVNA (LLOQ=20, grey shade). Asterisks indicate that results were statistically significant, as follows: *, P<0.05.
Figure 7:
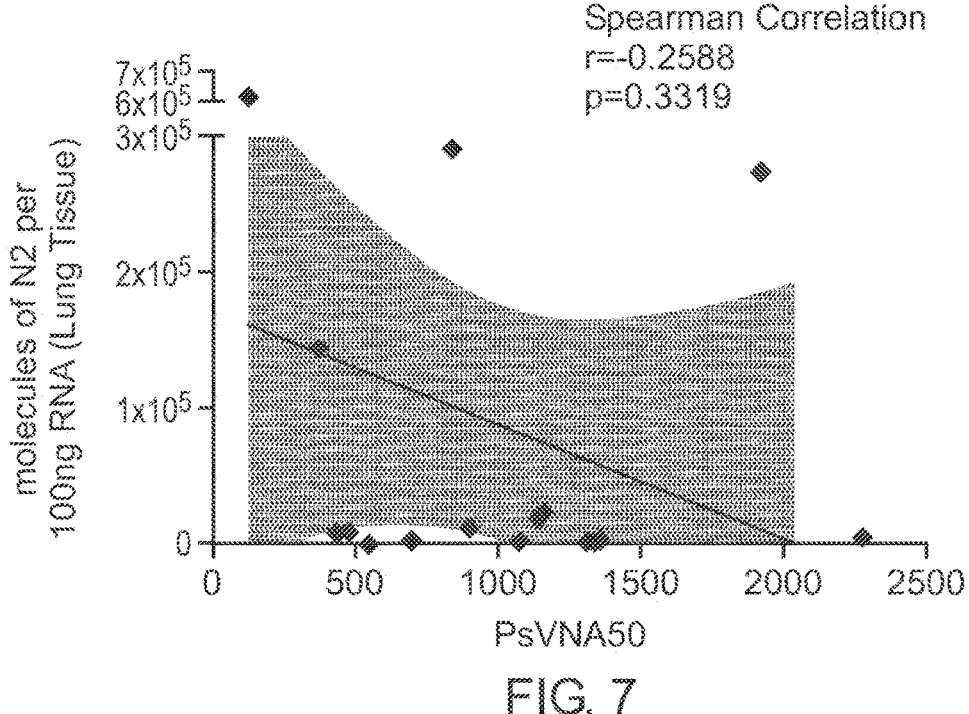
FIG. 7 depicts correlation of PsVNA50 titers and lung viral RNA. Fifty percent neutralization titers by PsVNA from hamsters vaccinated twice with nCoV-S(JET) vaccine are plotted against viral RNA detected in lung homogenates at the time of euthanasia. Correlation was analyzed by Spearman with an r=−0.2588 and P=0.3319 with linear regression (black line) and 95% confidence intervals (shaded area) shown.

Example 1: Evaluation of DNA Vaccine in Wild-Type Hamster Model of COVID-19 Disease A SARS-CoV-2 spike-based DNA vaccine, nCoV-S(JET), was constructed by cloning a human-codon-optimized gene encoding the full-length spike protein into a plasmid vector as described in Methods. The plasmid backbone used for this vaccine, pWRG, has been used for hantavirus DNA vaccines that are currently in phase 1 and 2 clinical trials (Brocato, R. L. & Hooper, J. W., *Viruses* 2019, 11(7): 610). Expression of the spike protein from the nCoV-S(JET) was confirmed to express in cell culture (FIGS. 3A-3B). In the first vaccine efficacy experiment, groups of 8 hamsters were vaccinated on week 0 and 3 with nCoV-S(JET), a MERS-CoV DNA vaccine, or PBS using jet injection (FIG. 1A). Sera were collected after 1 vaccination (Wk 3) or 2 vaccinations (Wk 5) and evaluated in a SARS-CoV-2 plaque reduction neutralization test (PRNT) and pseudovirion neutralization assay (PsVNA). SARS-CoV-2 virus neutralizing antibodies were detected in less than half of the animals after 1 vaccination, and in all of the animals by both assays after the boost (p=0.0156 (PRNT50), p=0.0078 (PsVNA50), Wilcoxon matched-pairs signed rank test FIG. 1B; PRNT80 and PsVNA80 titers shown in FIGS. 4A-4B). Results from the PRNT and PsVNA were acceptably similar (FIGS. 5A-5B). The MERS DNA vaccine did not elicit SARS-CoV-2 cross-neutralizing antibodies as measured by PRNT or PsVNA, but all of animals vaccinated with the vaccine developed MERS virus neutralizing antibodies as measured by PsVNA (FIG. 6).

Figure 1C:
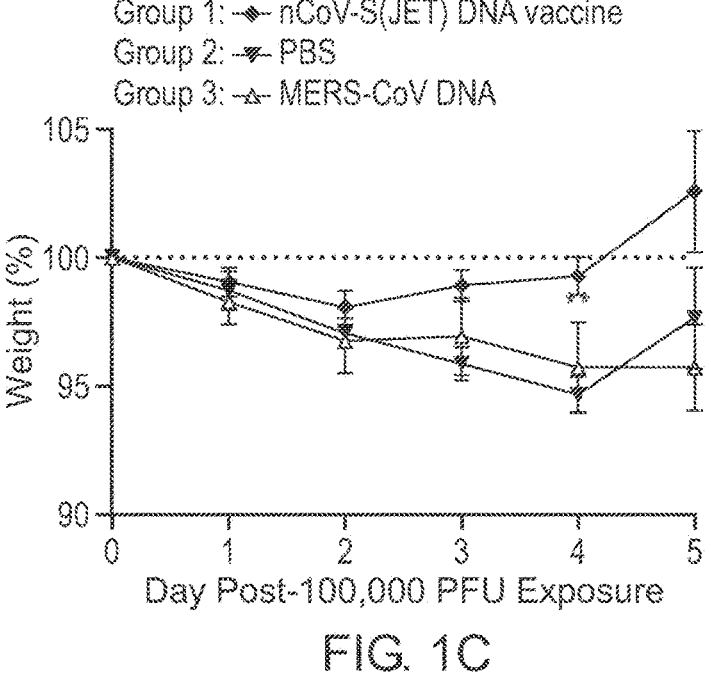
Figure 1D:
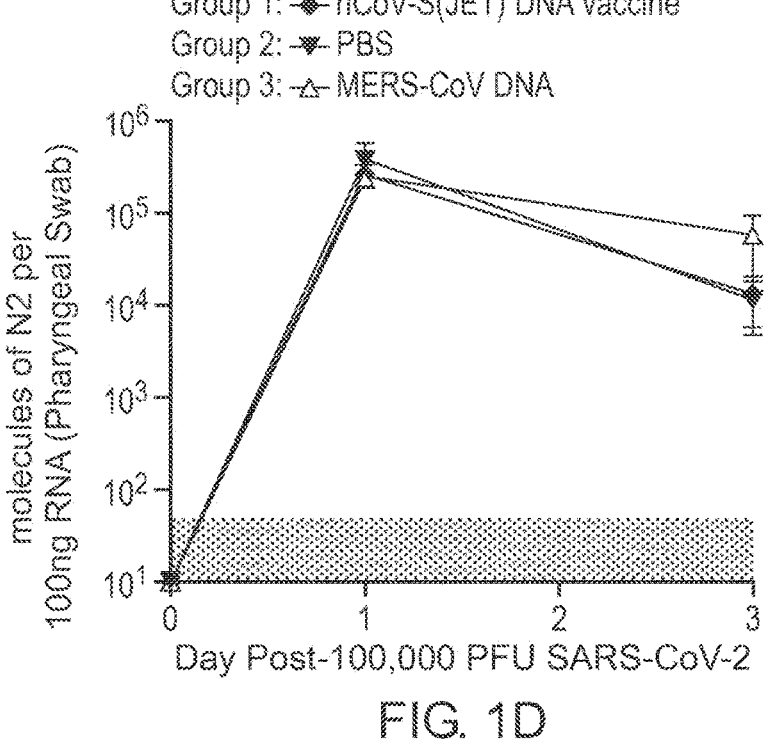
Figure 1E:
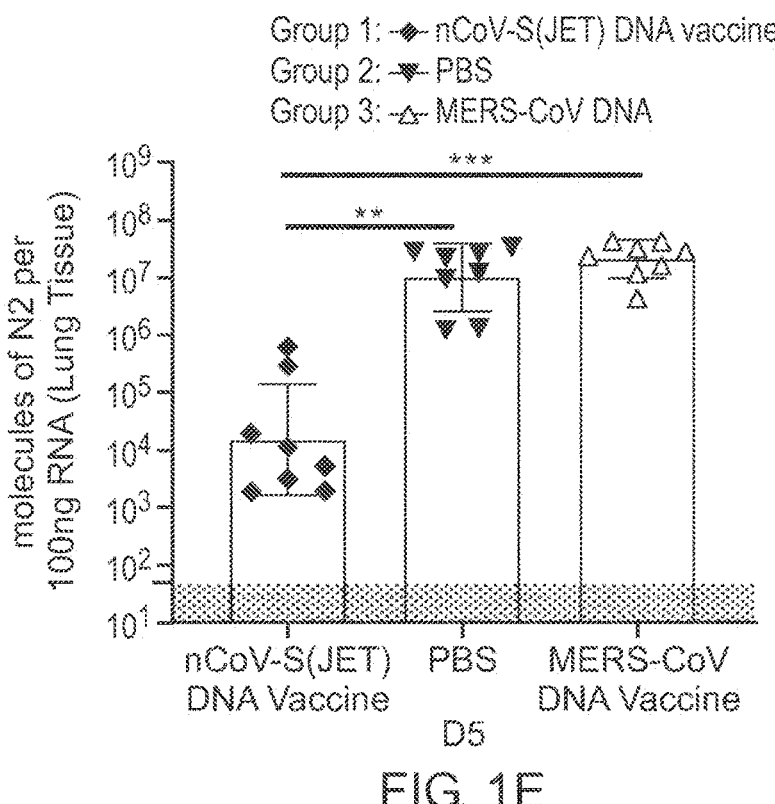
Figure 1F:
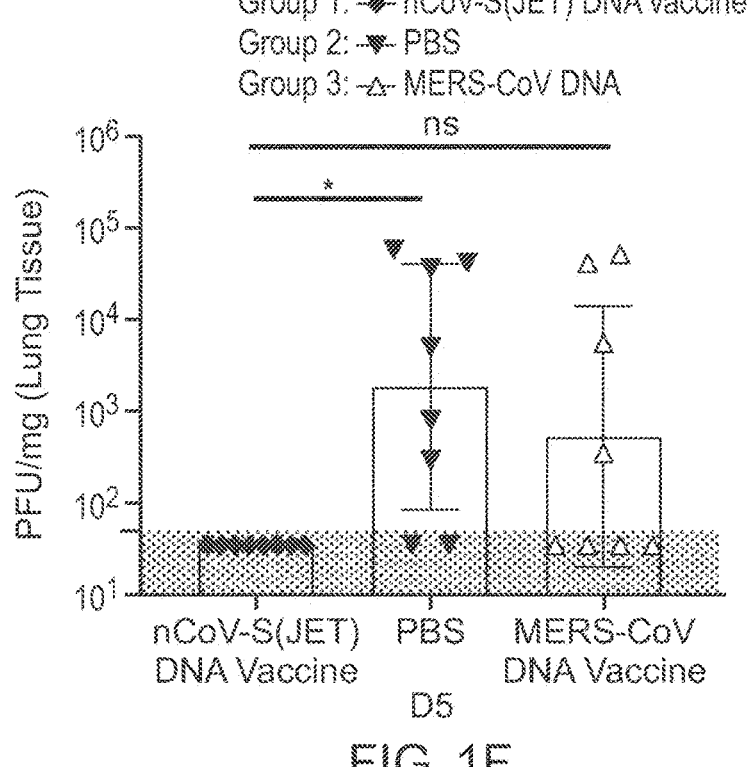
Figures 1G, 1H, 1I, 1J, 1K, 1L:
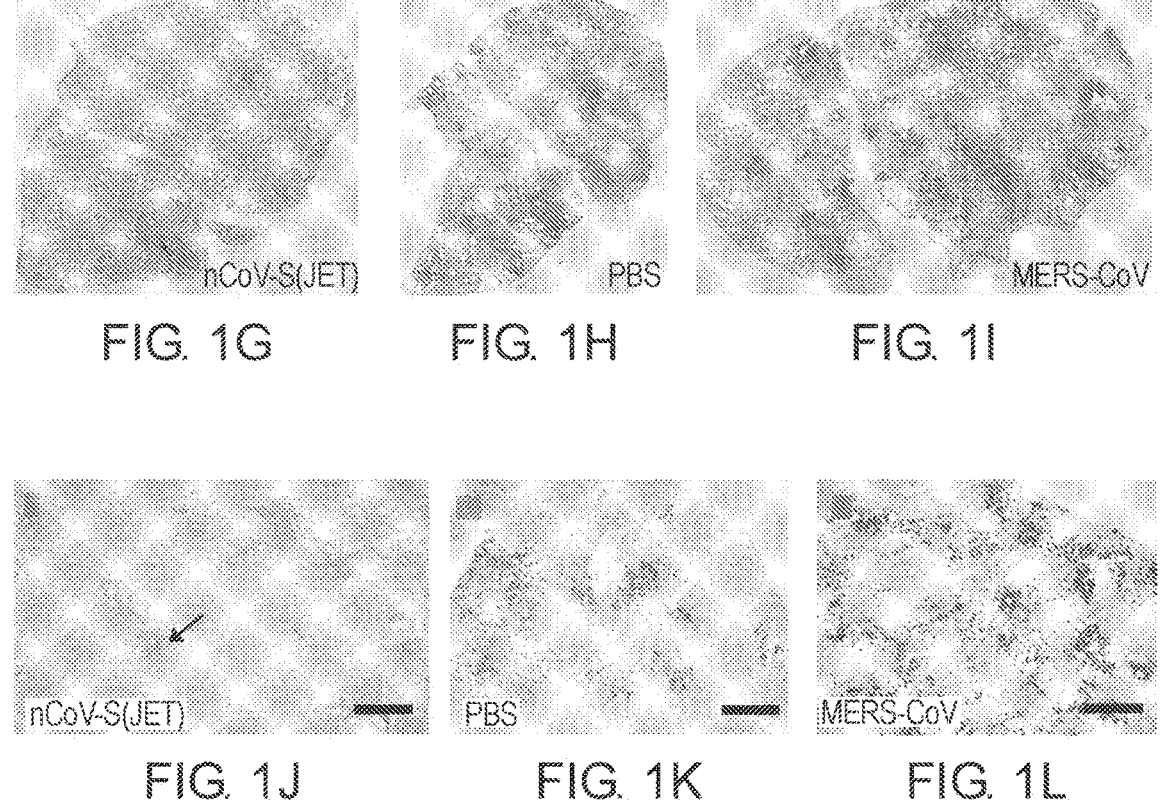

Three weeks after the boost all of the hamsters were exposed to 100,000 PFU SARS-CoV-2 by the intranasal route (Day 0). Daily weight change data demonstrated that animals vaccinated with nCoV-S(JET) lost significantly less weight than the animals vaccinated with the PBS control on Day 4 (p=0.0044, Kruskal-Wallis test, FIG. 1C). In contrast, animals vaccinated with the MERS-CoV DNA vaccine were not protected from weight loss. No significant changes in viral RNA from the pharyngeal swabs between nCoV-S (JET)-vaccinated and PBS animals were observed at any timepoint (FIG. 1D). Animals were euthanized 5 days after virus exposure and lung homogenates were assayed for the presence of viral RNA and infectious virus. There were significant reductions in viral RNA (p<0.0001, t-test, FIG. 1E) and infectious virus (p=0.0075, t-test, FIG. 1F) in the hamsters vaccinated with nCoV-S(JET) DNA when compared to the animals vaccinated with MERS-CoV DNA or PBS (control). Bright field imagery of lung H&E sections showed extensive areas of consolidation in the PBS- and MERS-CoV-vaccinated hamsters that are not observed in the nCoV-S(JET)-vaccinated hamsters (FIGS. 1G-1I). Multifocal and scattered positive labeling in areas of inflammation and respiratory epithelial cells is detected by ISH in PBS and MERS-CoV vaccinated hamsters that are not present in nCoV-S(JET) vaccinated hamsters (FIGS. 1J-1L). Together, these data indicate the nCoV-S(JET) vaccine had a protective effect in the Syrian hamster model.

Figure 2A:
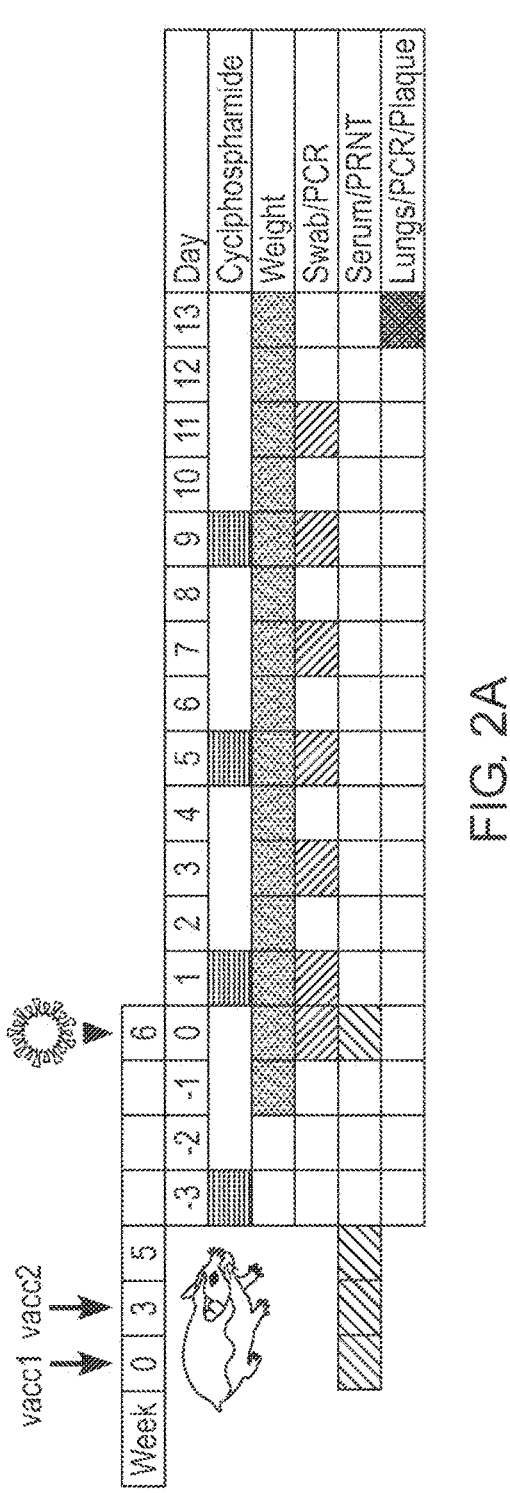
FIGS. 2A-2K depict evaluation of nCoV-S(JET) DNA vaccine in immunosuppressed Syrian hamsters.
Figure 2B:
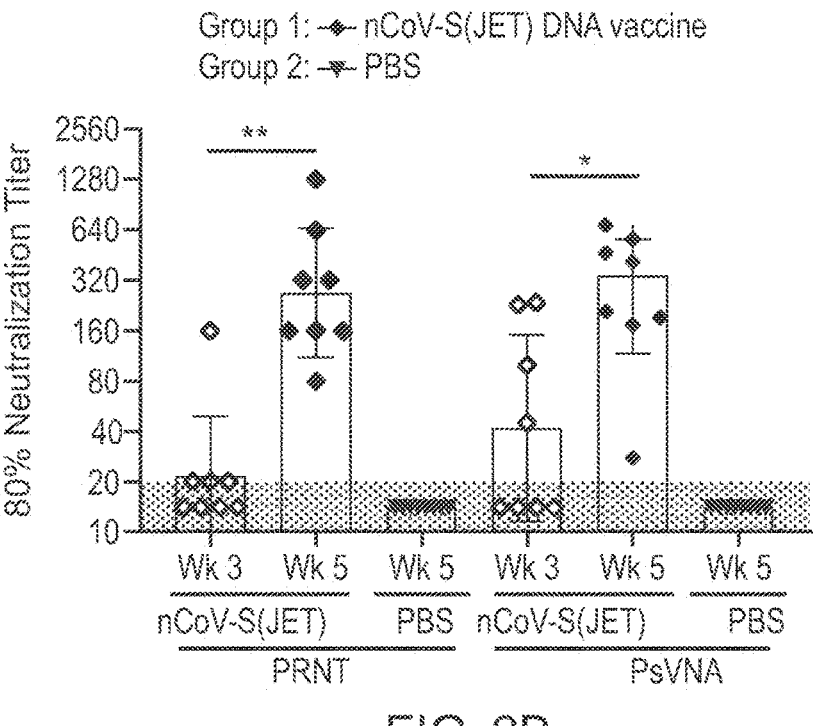

Example 2: Evaluation of DNA Vaccine in an Immunosuppressed Hamster Model of Severe COVID-19 Disease In a second vaccine efficacy experiment, groups of 8 hamsters were vaccinated on week 0 and 3 with nCoV-S (JET) or PBS using jet injection (FIG. 2A). Sera were collected after 1 vaccination (Wk 3) or 2 vaccinations (Wk 5) and evaluated in a SARS-CoV-2 PRNT and PsVNA (p=0.0078 (PRNT), p=0.0234 (PsVNA), Wilcoxon matched pairs signed rank test, FIG. 2B). Correlation of neutralization assays is shown in FIGS. 5A-5B. Neutralizing antibodies were detected in half the animals after 1 vaccination and in all of the animals by both assays after the boost (FIG. 2B). In contrast, hamsters vaccinated with PBS were negative for neutralizing antibodies in both assays.

Figure 2C:
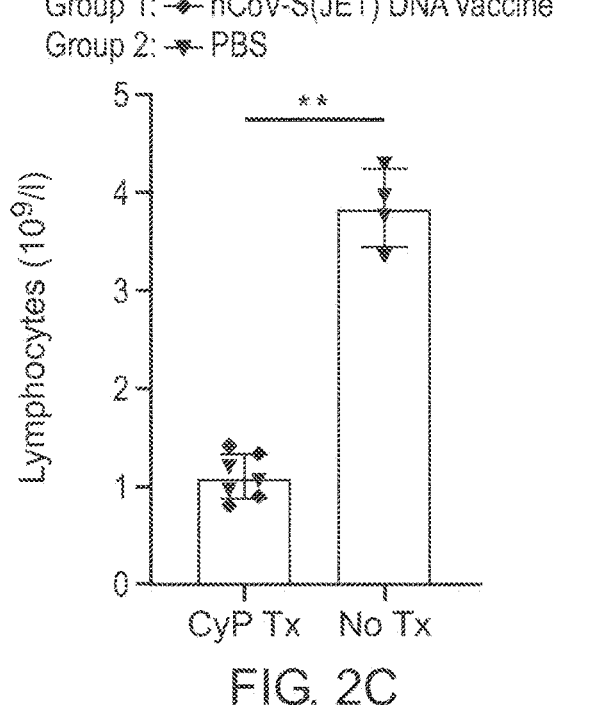
Figure 2D:
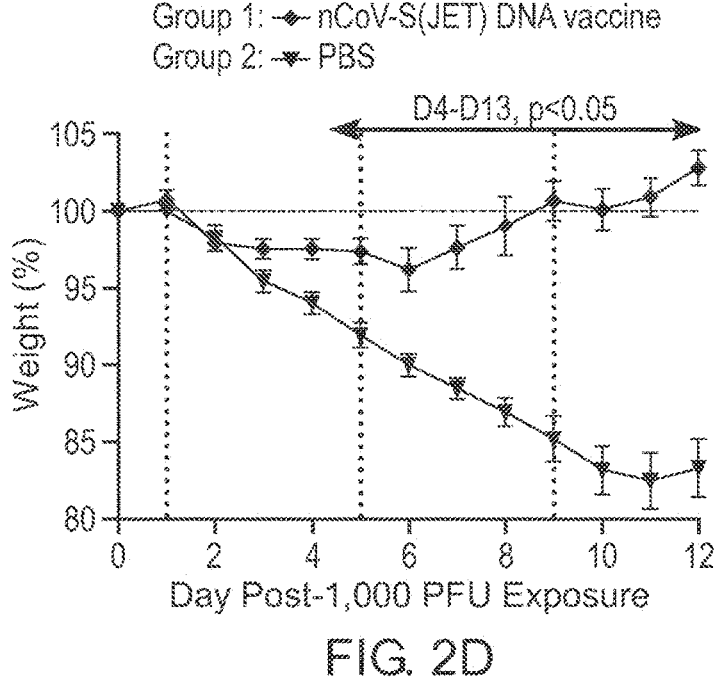
Figure 2E:
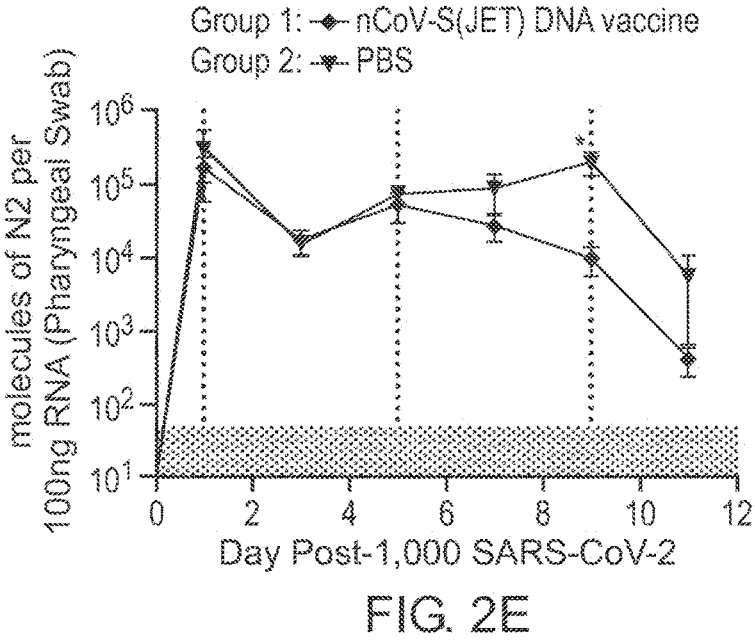
Figure 2F:
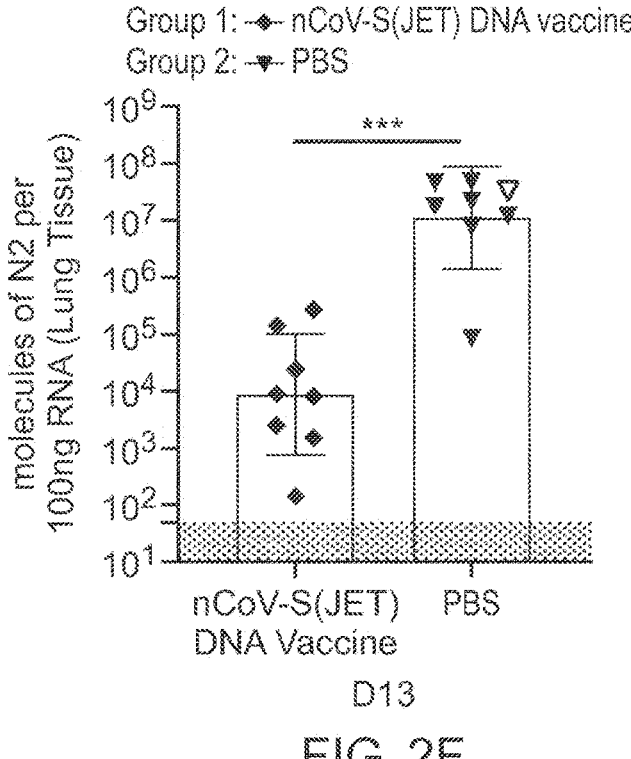
Figure 2G:
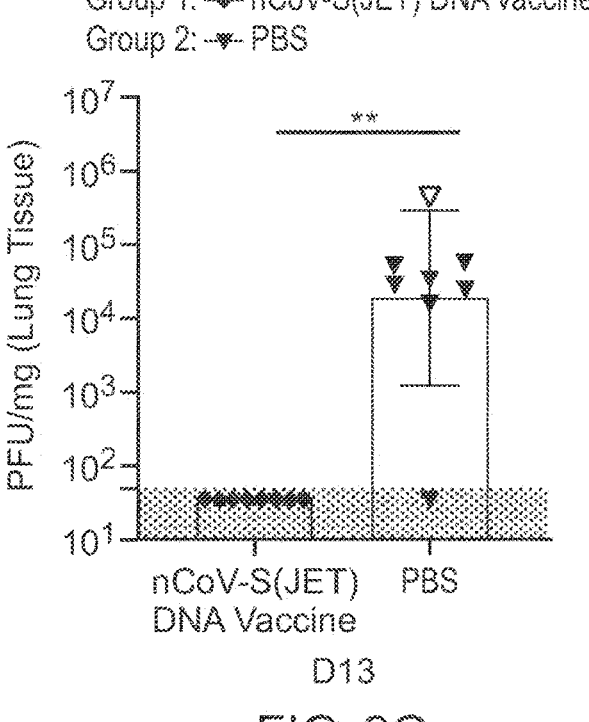
Figures 2H, 2I:
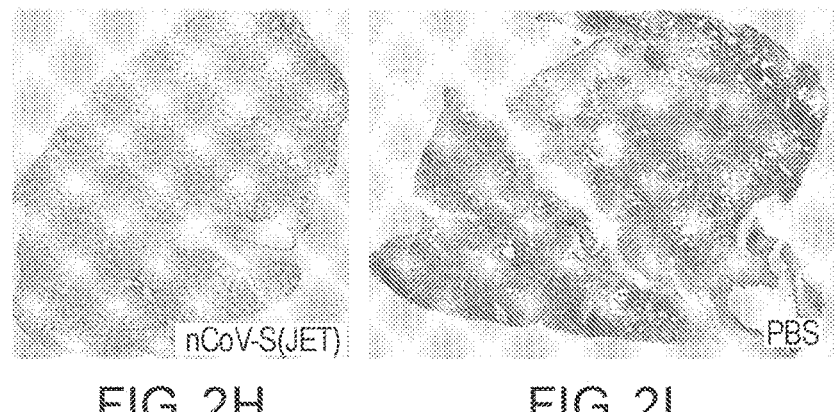
Figures 2J, 2K:
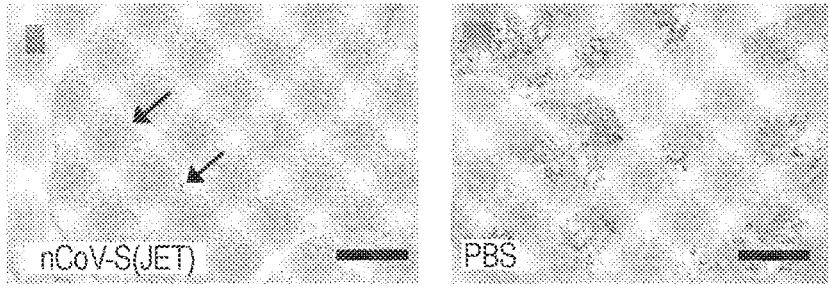

It was previously demonstrated that transient immunosuppression using CyP results in a severe disease model in Syrian hamsters (Brocato, R. L. et al., *J. Virol.* 2020, 94(22): e01683-20). Here, hamsters were treated with CyP on Day −3, 1, 5, and 9. On Day 0 prior to challenge, hamsters were bled for hematology to confirm lymphopenia (FIG. 2C). Hamsters were then exposed to 1,000 PFU SARS-CoV-2 virus by the intranasal route (Day 0). Starting on Day 4 post-infection and continuing through the rest of the experiment, significant differences in weight were observed between hamsters vaccinated with nCoV-S(JET) DNA versus PBS (Day 4, p=0.0059, Days 5-13, p<0.001, t-test, FIG. 2D). nCoV-S(JET) DNA-vaccinated hamsters had significantly less viral RNA in the pharyngeal swabs on Day 9 (p=0.0286, t-test, FIG. 2E), and the pharyngeal swabs were seen to trend lower on Days 7 and 11 for these animals. On Day 13 post-infection (termination of experiment), significant reductions in viral RNA (p=0.0006, t-test, FIG. 2F) and infectious virus (p=0.0014, t-test, FIG. 2G) in the lungs were measured between the nCoV-S(JET) DNA vaccine group and the PBS group. Similar pathology was noted in the transiently immunosuppressed hamsters compared to wild-type animals shown in FIGS. 1G-1L, with extensive areas of consolidation observed by H&E and multifocal and scattered positive labeling in areas of inflammation and respiratory epithelial cells by ISH (FIGS. 2H-21). Note that these lungs were collected on Day 13, whereas those collected in the experiment with wild-type hamsters were collected on Day 5. Together, these data indicate that the nCoV-S(JET) vaccine produces a protective effect in the transiently immunosuppressed hamster model before exposure to virus. Unprotected animals lost >15% of their weight and still harbored infectious virus in their lungs almost two weeks after exposure.

The COVID-19 pandemic has spurred an unprecedented global effort to develop a vaccine to prevent this disease. Nearly every conceivable vaccine platform has been brought to use to address the problem, including both RNA- and DNA-based vaccines. Nucleic acid vaccines can be produced rapidly once a target immunogen sequence is known; however, delivering the nucleic acid to cells for immunogen expression remains a technical challenge. For RNA vaccines, efficient vaccine delivery requires formulation with lipid nanoparticles (LNPs) or other modalities to protect the RNA and get it across cell membranes. The safety and efficacy of LNP-formulated RNA is currently being assessed in multiple COVID vaccine clinical trials (see e.g., Clinicaltrials.gov). DNA delivered by needle and syringe can be immunogenic without LNP formulation, even in nonhuman primates (Yu, J. et al., *Science* 2020, 369(6505): 806-811); however, the use of other techniques such as electroporation or jet injection can increase immunogenicity while reducing dosing requirements. At least one COVID-19 DNA vaccine delivered by electroporation (Inovio) has advanced into the clinic (Clinicaltrials.gov).

There have no reports of a COVID-19 DNA delivered by jet injection advancing into the clinical- or even progressed to animal efficacy testing. This is surprising because of the logistical and regulatory advantages of disposable syringe jet injection over electroporation. There are several contract manufacturing organizations around the world capable of rapidly producing GMP plasmid for use in humans. Thus, the drug substance could be produced rapidly and the safety profile for DNA vaccines has been established over decades. The drug product delivery system, disposable syringe jet injection, such as PharmaJet's Stratis, is U.S. FDA 510(k)-cleared and has CE Mark and WHO PQA certification. Disadvantages of the DNA vaccine is that at least one booster vaccination, and possibly two in humans, would likely be needed and the dosage would be milligrams rather than micrograms, as is the case for LNP-formulated mRNA vaccines.

There are a limited number of published reports of COVID-19 vaccine efficacy testing in animal models of COVID-19 disease. These include the testing of self-amplifying mRNA in the K18-hACE2 mouse model (de Alwis, R. et al., *bioRxiv* 2020, 2020.2009.2003.280446), a VSV-vectored vaccine in the hACE2 transduced mouse model (Case, J. B. et al., *Cell Host Microbe* 2020, 28: 465-474), and at least four virus-vectored (i.e., yellow fever, adenovirus, VSV, and inactivated Newcastle disease virus) vaccines in the SARS-CoV-2 adapted mouse and/or the Syrian hamster model (Felipe, L. S. et al., *bioRxiv*, 2020.2007.2008.193045; Yahalom-Ronen, Y. et al. bioRxiv, 2020.2006.2018.160655; Mercado, N. B. et al., *Nature* 2020, 586(7830): 583-588; and Sun W. et al., *Vaccines (Basel)* 2020, 8(4): 771). In all of the aforementioned efficacy experiments, the vaccines were based on the full-length spike protein and neutralizing antibodies were predictive of protection. The present disclosure describes a jet injection technique to deliver a SARS2 spike-based DNA vaccine to Syrian hamsters and rhesus macaques. Although jet injection technology is not widely available for small animal use, a human intradermal jet injection technology is employed herein to deliver vaccines intramuscularly to the hamsters. It was previously demonstrated that there would be approximately 300-fold increases in neutralizing antibodies when this jet injection technique was used relative to a needle and syringe in hamsters vaccinated with hantavirus DNA vaccines (Brocato, R. L. et al., *J. Virol.* 2020, 94(22): e01683-20).

The immunogenicity parameter focused upon in this disclosure was neutralizing antibody. Neutralizing antibodies against live virus were measured by PRNT and a VSV-based PsVNA. These assays showed significant correlation (p<0.0001) (FIGS. 5A-5B). The neutralizing antibody levels rose significantly after the booster vaccination reaching a PRNT80 geometric mean titer of 207 and PRNT50 GMT of 761 that are comparable or exceeding titers of other DNA vaccines evaluated in nonhuman primates (Yu, J. et al., *Science* 2020, 369(6505): 806-811) and mice (Smith, T. R. F. et al., *Nat. Commun.* 2020, 11(1): 2601). The PRNT50=761 is similar to the 50% titers elicited in hamsters vaccinated with single-dose, live-virus vectored vaccines: Ad26-vectored vaccine PsVNA50<1000; VSV-vectored vaccine PRNT50<1000, and Yellow Fever-vectored vaccine PRNT50<1000 (Chan, J. F. et al., *Clin Infect Dis*, 2020, 71(9): 2428-2446; Felipe, L. S. et al., bioRxiv, 2020.2007.2008.193045; and Tostanoski, L. H. et al., *Nature Medicine* 2020, 26: 1694-1700). Neutralization titer was plotted against viral RNA detected in lung tissue collected at the time of euthanasia. Negative correlation was observed (FIG. 7); however, this did not reach statistical significance. There was no cross-neutralizing antibodies against MERS pseudovirions, and those animals were not protected from disease in the hamster model.

The results in the transiently-immunosuppressed hamster model add extra credence to the idea that antibodies are playing an important role in the protection observed. The transient-immunosuppressed hamster model is a low-dose (1,000 PFU), severe disease model. CyP treatment of hamsters, renders B and T cells non-functional, essentially replicating an antibody passive transfer experiment where, rather than the passive transfer of exogenous antibody, the vaccine-generated antibody circulating in the animal prior to CyP treatment must be sufficient to protect against disease. If a candidate vaccine protects the animal prior to CyP treatment (the wild-type hamster model), but not in the transiently-immunosuppressed hamster model, then that would indicate that T and/or B cell proliferation is required for protection afforded by that vaccine. In the case of the nCoV-S(JET) DNA vaccine, normal T and/or B cell proliferation at the time of exposure was not necessary for the protective effect.

The present disclosure shows that a relatively simple unmodified full-length S DNA vaccine administered by a relatively simple jet injection technique can elicit neutralizing antibodies after a single vaccination, PRNT50 titers >700 after a booster, and protect in two hamster models of disease caused by SARS-CoV-2. The vaccine-mediated protection in the transiently-immunosuppressed hamster model provides additional insights into the mechanism of vaccine-mediated protection against SARS-CoV-2.

Example 3: Testing DNA Vaccine in Nonhuman Primates

Figure 8:
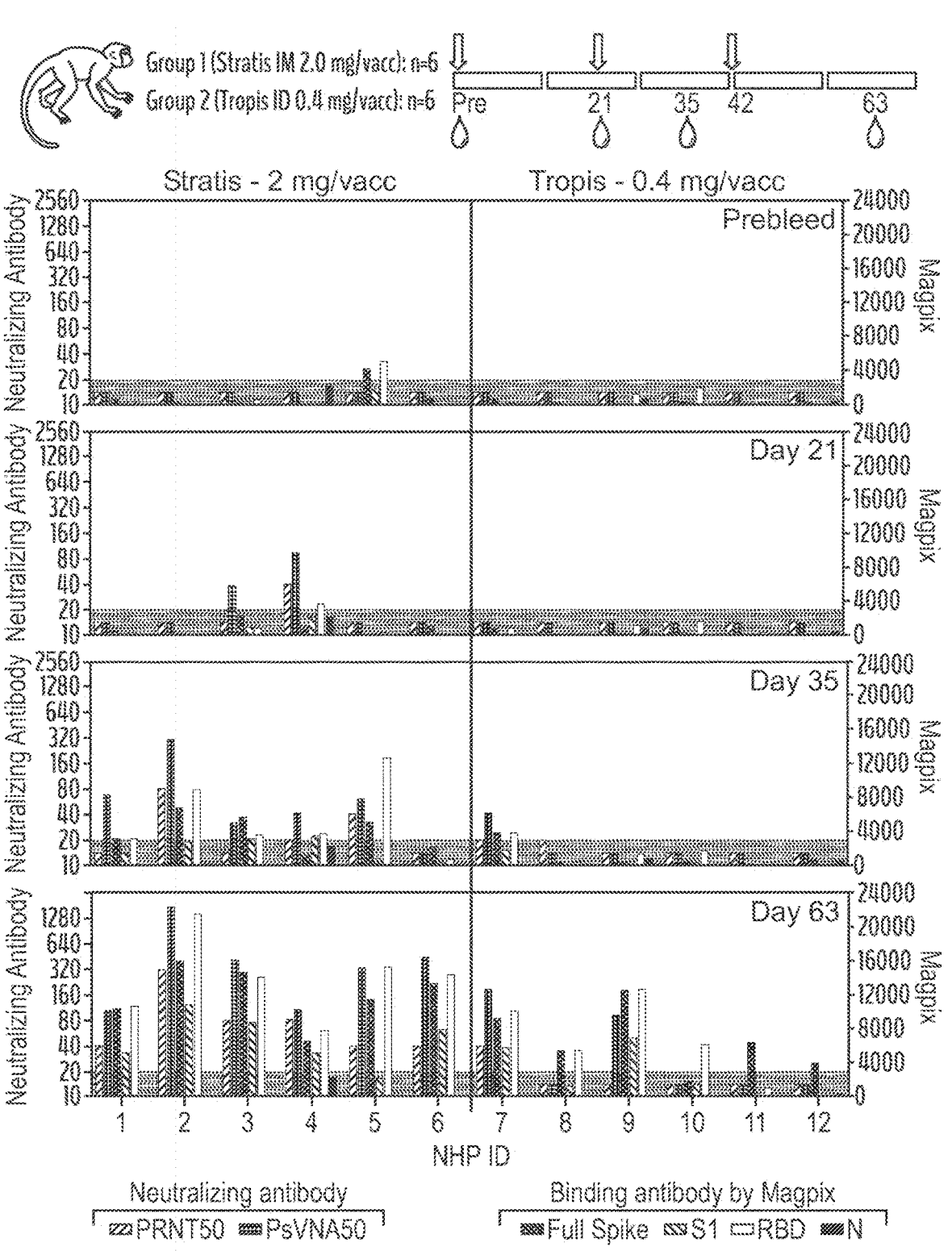
FIG. 8 depicts testing pWRG/nCoV-S(opt) in rhesus macaques, showing both the experimental design and the results of neutralizing antibody measurements and binding antibody measurements.

Groups of 6 rhesus macaques were vaccinated with the pWRG/nCoV-S(opt) DNA vaccine. Group 1 was vaccinated using the Stratis intramuscular (IM) needle-free jet injection device and Group 2 was vaccinated using the PharmaJet Tropis intradermal (ID) device. Group 1 received 2 mg of DNA per vaccination (2 administrations of 1 mg each). Group 2 received five times less DNA (0.4 mg) per vaccination (2 administrations of 0.2 mg each). Animals were vaccinated on Day 0, 21, and 42 days after the initial vaccination. Blood was collected before vaccination (pre) and on days 21, 35, and 63. Sera were run in two assays to measure neutralizing antibody: a pseudovirion neutralization assay (PsVNA) and a plaque reduction neutralization test (PRNT) using live virus (WA-1 isolate). The sera was also run in a magpix assay to measure binding antibody. Data are shown in FIG. 8. Overall, the animals vaccinated with the higher dose using the PharmaJet Stratis device developed more robust antibody responses. Five of six Group 1 animals developed neutralizing antibodies after two vaccinations. All of the Group 1 animals developed neutralizing antibodies after the third vaccination. Only two of the Group 2 animals developed neutralizing antibodies with a titer ≥40 after the third vaccination. In general, the binding antibodies trended with the neutralizing antibody responses.

While some embodiments have been shown and described herein, such embodiments are provided by way of example only. Numerous variations, changes, and substitutions will occur to those skilled in the art without departing from the compositions and materials described. It should be understood that various alternatives to the embodiments of the invention described herein can be employed in practicing the invention.

---

What is claimed is:

1. A severe acute respiratory syndrome coronavirus 2 (SARS-CoV-2) spike-based DNA composition comprising a recombinant DNA construct in a plasmid, wherein the recombinant DNA construct comprises SEQ ID NO: 1 as a human codon-optimized nucleic acid sequence encoding a SARS-CoV-2 spike protein.

2. The SARS-CoV-2 spike-based DNA composition of claim 1, further comprising a pharmaceutically acceptable carrier, stabilizer, and/or excipient.

3. The SARS-CoV-2 spike-based DNA composition of claim 1, further comprising an adjuvant.

4. The SARS-CoV-2 spike-based DNA composition of claim 3, wherein the adjuvant is a liposome-based adjuvant; a lipid nanoparticle (LNP); a saponin-based adjuvant made of nanometer particles, cholesterol, and phospholipid; or an oil-and-water emulsion with or without saponin.

5. A method of eliciting an immune response to a SARS-CoV-2 in a human subject, comprising administering to the human subject an effective amount of the SARS-CoV-2 spike-based DNA composition of claim 1.

6. The method of claim 5, wherein about 5.0 mg of the plasmid is administered to the human subject without any adjuvant, or about 0.5 mg of the plasmid is administered with an adjuvant.

7. The method of claim 5, wherein the SARS-CoV-2 spike-based DNA composition is administered to the human subject intramuscularly, subcutaneously, or intradermally.

8. The method of claim 7, wherein the SARS-CoV-2 spike-based DNA composition is administered to the human subject intramuscularly using a jet injector.

9. The method of claim 5, wherein the SARS-CoV-2 spike-based DNA composition is administered at least twice to the human subject.

10. The method of claim 8, wherein the SARS-CoV-2 spike-based DNA composition is administered to the human subject at least twice, wherein each administration is separated by at least four weeks.

11. The method of claim 5, wherein the SARS-CoV-2 spike-based DNA composition is administered as a booster shot.

12. The method of claim 11, wherein the human subject administered with the booster shot previously was administered with a SARS-CoV-2 spike-based DNA that differs from the SARS-CoV-2 spike-based DNA in the booster shot.

13. The method of claim 11, wherein the booster shot is administered to the human subject who previously was administered a SARS-CoV-2 mRNA vaccine, a SARS-CoV-2 adenovirus vaccine, or a SARS-CoV-2 protein vaccine.

14. The SARS-CoV-2 spike-based DNA composition of claim 1, wherein the DNA composition, when administered to a human subject after at least two administrations, elicits neutralizing antibody production in the human subject.

*    *    *    *    *